(12) United States Patent
Hoffman et al.

(10) Patent No.: US 6,921,526 B2
(45) Date of Patent: Jul. 26, 2005

(54) GASTRIN RECEPTOR-AVID PEPTIDE CONJUGATES

(75) Inventors: Timothy J. Hoffman, Columbia, MO (US); Wynn A. Volkert, Columbia, MO (US); Ning Li, Baltimore, MD (US); Gary Sieckman, Ashland, MO (US); Chrys-Ann Higginbotham, Columbia, MO (US)

(73) Assignee: Curators of the University of Missouri, Columbia, MO (US)

( * ) Notice: Subject to any disclaimer, the term of this patent is extended or adjusted under 35 U.S.C. 154(b) by 84 days.

(21) Appl. No.: 10/122,611

(22) Filed: Apr. 12, 2002

(65) Prior Publication Data

US 2002/0176819 A1 Nov. 28, 2002

Related U.S. Application Data

(60) Continuation of application No. 09/537,423, filed on Mar. 29, 2000, now abandoned, which is a division of application No. 09/064,499, filed on Apr. 22, 1998, now Pat. No. 6,200,546.
(60) Provisional application No. 60/044,049, filed on Apr. 22, 1997.

(51) Int. Cl.[7] .................. A61K 51/00; A61M 36/14
(52) U.S. Cl. .............. 424/1.69; 424/1.11; 424/1.65; 424/9.1; 530/300; 530/309
(58) Field of Search ............... 424/1.11, 1.65, 424/1.69, 9.1, 1.37, 9.3, 9.4, 9.5, 9.6, 9.7; 534/7, 10–16; 530/300, 333, 317, 309, 338, 324, 327; 206/569, 570; 514/14–16

(56) References Cited

U.S. PATENT DOCUMENTS

| | | | | |
|---|---|---|---|---|
| 4,988,496 A | * | 1/1991 | Srinivasan et al. | 424/1.11 |
| 5,428,019 A | * | 6/1995 | Edwards et al. | 514/16 |
| 5,686,410 A | * | 11/1997 | Albert et al. | 514/12 |
| 6,200,546 B1 | * | 3/2001 | Hoffman et al. | 424/9.1 |

OTHER PUBLICATIONS

Giblin et al (1998), Proc. Natl. Acad. Sci., USA, vol. 95, pp. 12814–12818.*

Walsh et al (1991), J. Med., vol. 155, pp. 152–163.*

* cited by examiner

*Primary Examiner*—Dameron L. Jones
(74) *Attorney, Agent, or Firm*—Kohn & Associates, PLLC

(57) ABSTRACT

A compound for use as a therapeutic or diagnostic radiopharmaceutical includes a group capable of complexing a medically useful metal attached to a moiety which is capable of binding to a gastrin releasing peptide receptor. A method for treating a subject having a neoplastic disease includes administering to the subject an effective amount of a radiopharmaceutical having a metal chelated with a chelating group attached to a moiety capable of binding to a gastrin releasing peptide receptor expressed on tumor cells with subsequent internalization inside of the cell. A method of forming a therapeutic or diagnostic compound includes reacting a metal synthon with a chelating group covalently linked with a moiety capable of binding a gastrin releasing peptide receptor.

28 Claims, 22 Drawing Sheets

HPLC CHROMATOGRAM OF RHODIUM-BBN-37
$^{105}RhCl_2$-BBN-37

HPLC CHROMATOGRAM OF RHODIUM-BBN-37
$RhCl_2$-BBN-37

GASTRIN RECEPTOR-AVID PEPTIDE CONJUGATES

Continuation Application of U.S. application Ser. No. 09/537,423 filed Mar. 29, 2000 now abandoned, which is a Divisional application of U.S. application Ser. No. 09/064,499 filed Apr. 22, 1998, now U.S. Pat. No. 6,200,546 incorporated herein by reference.

This application is based on Provisional Application which was filed on Apr. 22, 1997, Ser. No. 60/044,049.

GRANT REFERENCE

The research carried out in connection with this invention was supported in part by a grant from the Department of Energy (DOE), grant number DE-FG02-89ER60875, a grant from the U.S. Department of Veterans Affairs Medical Research Division and the Department of Radiology MU-C2-02691. The Government has certain rights in the invention.

TECHNICAL FIELD

This invention relates to radionuclide-labeled compounds useful as radiopharmaceuticals. More particularly, the present invention relates to conjugates of bombesin (BBN) analogues and a metal complexing group which, when complexed to a radionuclide, are useful therapeutic and imaging agents for cancer cells that express gastrin releasing peptide (GRP) receptors.

BACKGROUND OF THE INVENTION

Detection and treatment of cancers using radiopharmaceuticals that selectively target cancers in human patients has been employed for several decades. Unfortunately, only a limited number of site-directed radiopharmaceuticals that exhibit highly specific in vivo localization in or near cancer cells are currently in routine use, as being approved by the United States Food and Drug Administration (FDA). There is a great deal of interest in developing new radioactive drugs due to the emergence of more sophisticated biomolecular carriers that have high affinity and high specificity for in vivo targeting of tumors. Several types of agents are being developed and have been investigated including monoclonal antibodies (MAbs), antibody fragments ($F_{AB}$'s and ($F_{AB}$)$_2$'s), receptor-avid peptides [Bushbaum, 1995; Fischman et al., 1993; Schubiger et al. 1996].

The potential utility of using radiolabeled receptor-avid peptides for producing radiopharmaceuticals is best exemplified by $^{111}$In-DTPA-conjugated octreotide (an FDA approved diagnostic imaging agent, Octreoscan®, marketed in the United States. by Mallinckrodt Medical, Inc.) [Lowbertz et al. 1994]. This radiopharmaceutical is an $^{111}$In-DTPA conjugate of Octreotide, a small peptide analogue of the human hormone somatostatin. This drug specifically binds to somatostatin receptors that are over-expressed on neuroendocrine cancers (e.g., carcinoid Ca, neuroblastoma, etc.) as well as others [Krenning et al., 1994]. Since indium-111 ($^{111}$In) is not the ideal radionuclide for scintigraphic imaging, other somatostatin analogues and other receptor-avid biomolecules that are labeled with $^{99m}$Tc (the optimal radionuclide for diagnostic imaging) are being studied and developed [Eckelman, 1995; Vallabhajosula et al., 1996].

Bombesin (BBN) is a 14 amino acid peptide that is an analogue of human gastrin releasing peptide (GRP) that binds to GRP receptors with high specificity and has an affinity similar to GRP [Davis et al., 1992]. GRP receptors have been shown to be over-expressed or uniquely expressed on several types of cancer cells. Binding of GRP receptor agonists (also autocrine factors) increases the rate of cell division of these cancer cells. For this reason, a great deal of work has been, and is being pursued to develop BBN or GRP analogues that are antagonists [Davis et al., 1992; Hoffken, 1994; Moody et al., 1996; Coy et al., 1988; Cai et al., 1994]. These antagonists are designed to competitively inhibit endogenous GRP binding to GRP receptors and reduce the rate of cancer cell proliferation [Hoffken, 1994]. Treatment of cancers using these antagonists with these non-radioactive peptides requires chronic injection regimens (e.g., daily, using large quantities of the drug).

In designing an effective receptor-avid radiopharmaceutical for use as a diagnostic or therapeutic agent for cancer, it is important that the drug have appropriate in vivo targeting and pharmacokinetic properties [Fritzberg et al., 1992; Eckelman et al., 1993]. For example, it is essential that the radiolabeled receptor-avid peptide have high specific uptake by the cancer cells (e.g., via GRP receptors). In addition, it is necessary that once the radionuclide localizes at a tumor site, it must remain there for an extended time to deliver a highly localized radiation dose to the tumor. In order to achieve sufficiently high specific uptake of radiolabeled BBN analogues in tumors, the binding affinity of promising derivatives must be high (i.e., $K_d \cong 1$–5 nmolar or less) with prolonged retention of radioactivity [Eckelman et al., 1995; Eckelman, et al., 1993]. Work with $^{125}$I-BBN derivatives has shown, however, that for cancer cells that bind the $^{125}$I-BBN derivatives (whether they be agonists or antagonists), the radioactivity is either washed off or expelled from the cells (in vitro) at a rapid rate [Hoffman et al., 1997]. Thus, these types of derivatives have a low probability of remaining "trapped" at the tumor site (in vivo) sufficiently long to be effective therapeutic or diagnostic agents.

Developing radiolabeled peptides that are cleared efficiently from normal tissues is also an important and especially critical factor for therapeutic agents. When labeling biomolecules (e.g., MAb, $F_{AB}$'s or peptides) with metallic radionuclides (via a chelate conjugation), a large percentage of the metallic radionuclide (in some chemical form) usually becomes "trapped" in either the kidney or liver parenchyma (i.e., is not excreted into the urine or bile) [Duncan et al., 1997; Mattes, 1995]. For the smaller radiolabeled biomolecules (i.e., peptides or $F_{AB}$'s), the major route of clearance of activity is through the kidneys which in turn retain high levels of the radioactive metal (i.e., normally >10–15% of the injected dose) [Duncan et al., 1997]. This presents a major problem that must be overcome in the development of therapeutic agents that incorporate metallic radionuclides, otherwise the radiation dose to the kidneys would be excessive. For example, $^{111}$In-octreotide, the FDA approved diagnostic agent, exhibits high uptake and retention in kidneys of patients [Eckelman et al., 1995]. Even though the radiation dose to the kidneys is higher than desirable, it is tolerable in that it is a diagnostic radiopharmaceutical (it does not emit alpha- or beta-particles), and the renal dose does not produce observable radiation induced damage to the organ.

It has now been found that conjugating BBN derivatives which are agonists in non-metallated conjugates whichthat exhibit binding affinities to GRP receptors that are either similar to or approximately an order of magnitude lower than the parent BBN derivative. [Li et al., 1996a] These data coupled with our recent results show that it is now possible to add radiometal chelates to BBN analogues, which are agonists, and retain GRP receptor binding affinities that are sufficiently high (i.e., approx. 1–5 nmolar $K_d$'s) for further development as potential radiopharmaceuticals. These agonist conjugates are transported intracellularly after binding to cell surface GRP receptors and retained inside of the cells for extended time periods. In addition, in vivo studies in normal mice have shown that retention of the radioactive metal in the kidneys was low (i.e., <5%) with the majority of the radioactivity excreted into the urine.

According to one aspect of the present invention, there is provided a BBN conjugate consisting of essentially a radiometal chelate covalently appended to the receptor binding region of BBN [e.g., BBN(8–14)] to form radiolabeled BBN analogues that have high specific binding affinities with GRP receptors. These analogues are retained for long times inside of GRP expressing cancer cells. Furthermore, their clearance from the bloodstream, into the urine with minimal kidney retention, is efficient. Preferably, the radiometals are selected from $^{99m}Tc$, $^{186/188}Re$, $^{105}Rh$, $^{153}Sm$, $^{166}Ho$, $^{90}Y$ or $^{199}Au$, all of which hold the potential for diagnostic (i.e., $^{99m}Tc$) or therapeutic (i.e., $^{186/188}Re$, $^{105}Rh$, $^{153}Sm$, $^{166}Ho$, $^{90}Y$, and $^{199}Au$) utility in cancer patients [Schubiger et al, 1996; Eckelman, 1995; Troutner, 1978].

SUMMARY OF THE INVENTION

In accordance with the present invention, there is provided a compound for use as a therapeutic or diagnostic radiopharmaceutical which includes a group which is capable of complexing a metal attached to a moiety capable of binding to a gastrin releasing peptide receptor.

Additionally, in accordance with the present invention, a method for treating a subject having a neoplastic disease which includes the step of administering to the subject an effective amount of a radiopharmaceutical having a metal chelated with a chelating group attached to a moiety capable of binding to a gastrin releasing peptide receptor on a cancer cell, subsequently intracellularly transported and residualized inside the cell, is disclosed.

Additionally, in accordance with the present invention, a method of forming a therapeutic or diagnostic compound including the step of reacting a metal synthon with a chelating group covalently linked with a moiety capable of binding a gastrin releasing peptide receptor is disclosed.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
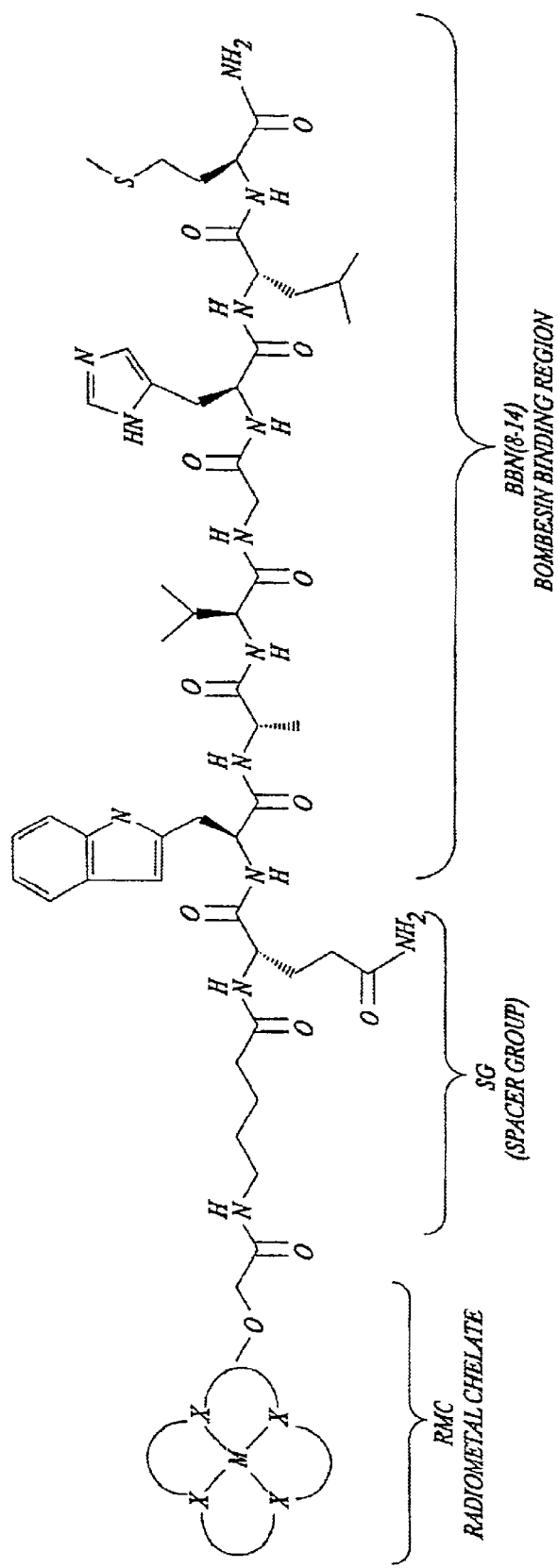
FIG. 1 illustrates a radiometal conjugate according to the present invention.

According to the present invention, compounds for use as diagnostic and/or therapeutic radiopharmaceuticals include a group capable of completing a metal attached to a moiety capable of binding to a gastrin releasing peptide (GRP) receptor as shown in FIG. 1. The moiety capable of specific binding to the GRP receptor is a GRP agonist. A GRP agonist would activate or produce response by the GRP receptor upon interaction with the GRP receptor and would be subsequently internalized inside of the cell by endocytosis. In contrast, a GRP antagonist would counteract the effect of an agonist and would not be internalized inside of the cell.

More specifically, the GRP agonist is a compound such as selected amino acid sequences or peptidomimetics which are known to activate the cell following binding with high affinity and selectivity to GRP receptors and that can be covalently linked to the metal complexing group. Many examples of specific modifications of the BBN(8–14) that can be made to produce sequences with high antagonistic and agonistic binding affinity for GRP repectors have been reported by numerous investigations [Davis et al., 1992; Hoffken, 1994; Moody et al., 1996; Coy et al., 1988; Cai et al., 1994; Moody et al., 1995; Leban et al., 1994; Cai et al., 1992].

In a preferred embodiment of the present invention, the metal complexing group or moiety is a chelating agent or chelator which complexes to metals such as $^{105}$Rh—, $^{186/188}$Re—, $^{99m}$Tc, $^{153}$Sm, $^{166}$Ho, $^{90}$Y or $^{199}$Au. The chelating agent or chelator is attached or bound to the GRP agonist "binding region" to produce a conjugate that retains its capability for high affinity and specific binding to GRP receptors.

In a more preferred embodiment of the present invention, the GRP agonist is a bombesin (BBN) analogue and/or a derivative thereof. The BBN derivative or analog thereof preferably contains either the same primary structure of the BBN binding region [i.e., BBN(8–14)] or similar primary structures, with specific amino acid substitutions, that will specifically bind to GRP receptors with better or similar binding affinities as BBN alone (i.e., $K_d \cong 1-5$ nmolar) Compounds containing this BBN binding region (or binding moiety), when covalently linked to other groups (e.g., a radiometal chelate), are also referred to as BBN conjugates.

In general, the compounds of the present invention have a structure of the general formula:

X—Y—B wherein X is a group capable of complexing a metal, such as a radiometal; Y is a covalent bond on a spacer group; and B is a bombesin agonist binding moiety.

The metal bound to the metal complexing group can be any suitable metal chosen for a specific therapeutic or diagnostic use including transition metals and γ and β emitting isotopes. Preferably, the metal is a radiometal such as $^{105}$Rh—, $^{99m}$Tc—, $^{186/188}$Re, $^{153}$Sm—, $^{166}$Ho—, $^{90}$Y—, and $^{199}$Au—whose chelates can be covalently linked (i.e., conjugated) to the specific BBN binding region via the N-terminal end of the primary binding sequence (e.g., BBN-8 or Trp$^8$) as shown in FIG. 1.

In a preferred embodiment, the radiometal complexes are positioned by being spaced apart from or remotely from the amino acid Trp$^8$ by the spacer groups. The spacer groups can include a peptide (i.e., ≧1 amino acid in length), a hydrocarbon spacer of $C_1$–$C_{10}$ or a combination of thereof. Preferably, the hydrocarbon spacer has is a $C_3$–$C_9$ group. The resulting radio-labeled BBN conjugates retain high binding affinity and specificity for GRP receptors and are subsequently internalized inside of the cell.

The BBN conjugates can further incorporate a spacer group or component to couple the binding moiety to the metal chelator (or metal binding backbone) while not adversely affecting either the targeting function of the BBN-binding moiety or the metal complexing function of the metal chelating agent.

The term "spacer group" or "linker" refers to a chemical group that serves to couple the BBN binding moiety to the metal chelator while not adversely affecting either the targeting function of the BBN binding moiety or the metal complexing function of the metal chelator. Suitable spacer groups include peptides (i.e., amino acids linked together) alone, a non-peptide group (e.g., hydrocarbon chain) or a combination of an amino acid sequence and a non-peptide spacer. The type of spacer group used in most of the experimental studies described below in the Examples section were composed of a combination of L-glutamine and hydrocarbon spacers. A pure peptide spacer could consist of a series of amino acids (e.g., diglycine, triglycine, gly-gly-glu, etc.), in which the total number of atoms between the N-terminal residue of the BBN binding moiety and the metal chelator in the polymeric chain is ≦12 atoms.

The spacer can also include a hydrocarbon chain [i.e., $R_1$—$(CH_2)_n$—$R_2$] wherein n is 0–10, preferably n=3 to 9, $R_1$ is a group (e.g., $H_2N$—, HS—, —COOH) that can be used as a site for covalently linking the ligand backbone or the preformed metal chelator or metal complexing backbone; and $R_2$ is a group that is used for covalent coupling to the N-terminal $NH_2$-group of the BBN binding moiety (e.g., $R_2$ is an activated COOH group). Several chemical methods for conjugating ligands (i.e., chelators) or preferred metal chelates to biomolecules have been well described in the literature [Wilbur, 1992; Parker, 1990; Hermanson, 1996; Frizberg et al., 1995]. One or more of these methods could be used to link either the uncomplexed ligand (chelator) or the radiometal chelate to the spacer group or to link the spacer group to the BBN(8–14) derivatives. These methods include the formation of acid anhydrides, aldehydes, arylisothiocyanates, activated esters, or N-hydroxysuccinimides [Wilbur, 1992; Parker, 1990; Hermanson, 1996; Frizberg et al., 1995].

Figure 2:
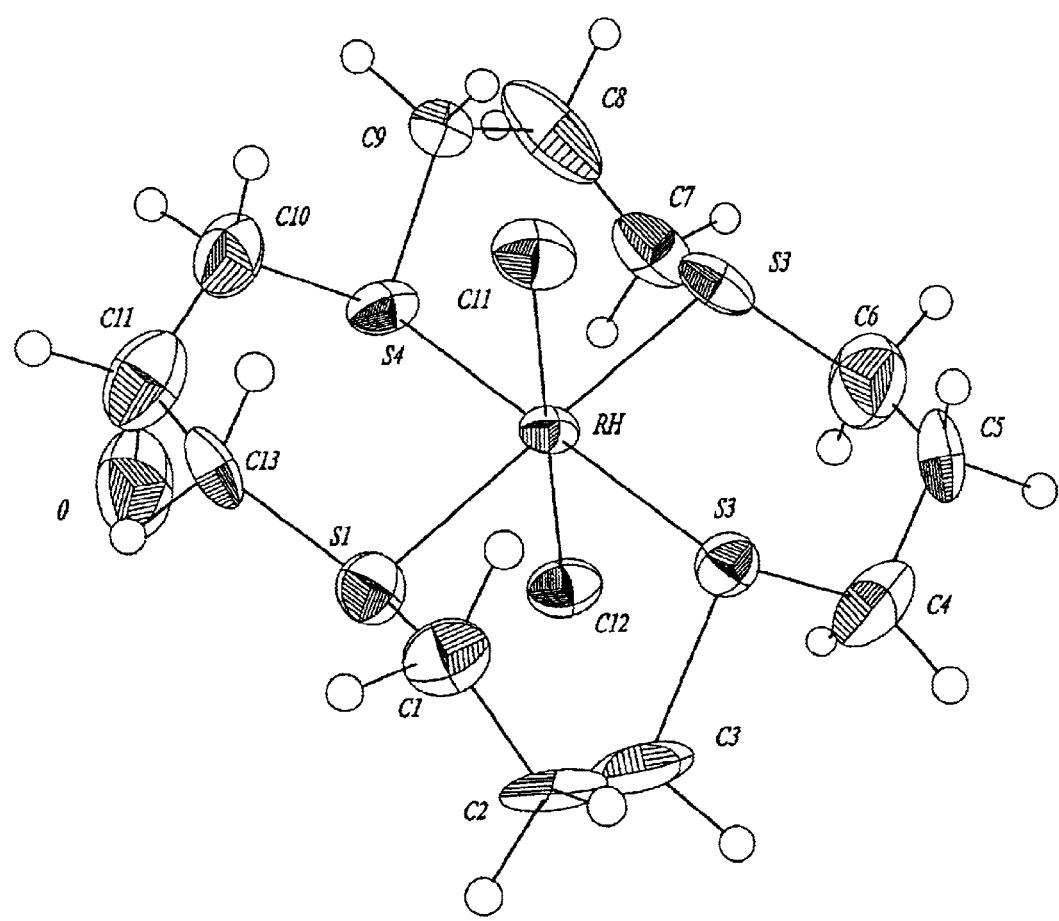
FIG. 2 is an ORTEP drawing of the {Rh[16]aneS$_4$-olCl$_2$}$^+$, illustrating the crystal structure a Rhodium macrocycle.

The term "metal complexing chelator" refers to a molecule that forms a complex with a metal atom that is stable under physiological conditions. That is, the metal will remain complexed to the chelator backbone in vivo. More particularly, a metal complexing chelator is a molecule that complexes to a radionuclide metal to form a metal complex that is stable under physiological conditions and which also has at least one reactive functional group for conjugation with the BBN agonist binding moiety. Metal complexing chelators can include monodentate and polydentate chelators [Parker, 1990; Frizberg et al., 1995; Lister-James et al., 1997; Li et al., 1996b; Albert et al., 1991; Pollak et al., 1996; de Jong et al., 1997; Smith et al., 1997]. Metal complexing chelators include tetradentate metal chelators which can be macrocyclic and have a combination of four nitrogen and/or sulphur metal-coordinating atoms [Parker et al., 1990; Li et al., 1996b] and are designated as $N_4$, $S_4$, $N_3S$, $N_2S_2$, $NS_3$, etc. as shown in FIG. 2. A number of suitable multidentate chelators that have been used to conjugate proteins and receptor-avid molecules have been reported [Frizberg et al., 1995; Lister-James et al., 1997; Li et al., 1996b; Albert et al., 1991; Pollak et al., 1996; de Jong et al., 1997]. These multidentate chelators can also incorporate other metal-coordinating atoms such as oxygen and phosphorous in various combinations. The metal binding complexing moiety can also include "3-1" chelators [Seifert et al., 1998].

For diagnostic purposes, metal complexing chelators preferably include chelator backbones for complexing the radionuclide metal $^{99m}$Tc. For therapeutic purposes, metal complexing chelators preferably include chelator backbones that complex the radionuclide Metals $^{105}$Rh, $^{186/188}$Re, $^{153}$Sm, $^{90}$Y, $^{166}$Ho, and $^{199}$Au [Schubiger et al., 1996; Hoffken, 1994].

As was briefly described above, the term "bombesin agonist" or "BBN agonist" refers to compounds that bind with high specificity and affinity to GRP receptors, and upon binding to the GRP receptor, are intracellularly internalized. Suitable compounds include peptides, peptidomimetics and analogues and derivatives thereof. In particular, previous work has demonstrated that the region on the BBN peptide structure required for binding to GRP receptors spans from residue 8 through 14 [Davis et al., 1992; Hoffken, 1994; Moody et al., 1996; Coy, 1988; Cai et al., 1994]. The presence of methionine (Met) at position BBN-14 will generally confer agonistic properties while the absence of this residue at BBN-14 generally confers antagonistic properties [Hoffken, 1994].

It is well documented in the art that there are a few and selective number of specific amino acid substitutions in the BBN (8–14) binding region (e.g., D-Ala$^{11}$ for L-Gly$^{11}$ or D-Trp$^8$ for L-Trp$^8$), which can be made without decreasing binding affinity [Leban et al., 1994; Qin et al., 1994; Jensen et al., 1993]. In addition, attachment of some amino acid chains or other groups to the N-terminal amine group at position BBN-8 (i.e., the Trp$^8$ residue) can dramatically decrease the binding affinity of BBN analogues to GRP receptors [Davis et al., 1992; Hoffken, 1994; Moody et al., 1996; Coy, et al., 1988; Cai et al., 1994]. In a few cases, it is possible to append additional amino acids or chemical moieties without decreasing binding affinity. The effects of conjugating various side chains to BBN-8 on binding affinity, therefore, is not predicable.

The BBN conjugates of the present invention can be prepared by various methods depending upon the selected chelator. The peptide portion of the conjugate can be most conveniently prepared by techniques generally established and known in the art of peptide synthesis, such as the solid-phase peptide synthesis (SPPS) approach. Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (tBoc) or a fluorenylmethoxycarbonyl (FMOC) group. The amino protecting group is removed with suitable deprotecting agents such as TFA in the case of tBOC or piperidine for FMOC and the next amino acid residue (in N-protected form) is added with a coupling agent such as dicyclocarbodiimide (DCC). Upon formation of a peptide bond, the reagents are washed from the support. After addition of the final residue, the peptide is cleaved from the support with a suitable reagent such as trifluoroacetic acid (TFA) or hydrogen fluoride (HF).

The spacer groups and chelator components are then coupled to form a conjugate by reacting the free amino group of the Trp$^8$ residue of the BBN binding moiety with an appropriate functional group of the chelator, metal chelator or spacer group, such as a carboxyl group or activated ester.

The BBN conjugate can also incorporate a metal complexing chelator backbone that is peptidic and compatible with solid-phase peptide synthesis. In this case, the chelator backbone can be added to the BBN binding moiety in the same manner as described above or, more conveniently, the metal complexing chelator backbone coupled to the BBN binding moeity can be synthesized in toto starting from the C-terminal residue of the peptide and ending with the N-terminal residue of the metal complexing chelator structure.

Figure 3:
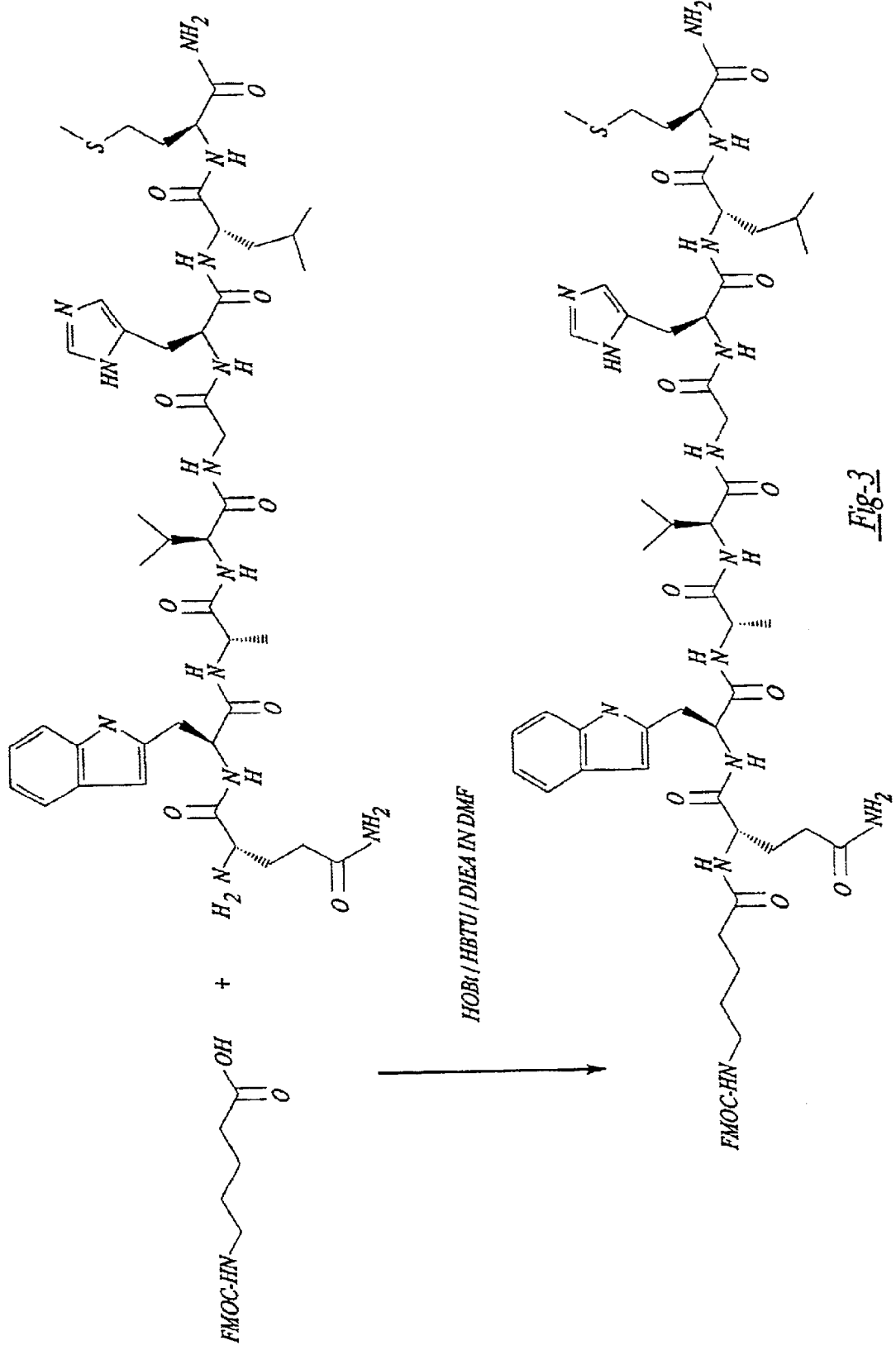
FIG. 3 illustrates a coupling reaction wherein a spacer group is coupled to a bombesin agonist binding moiety.
Figure 4:
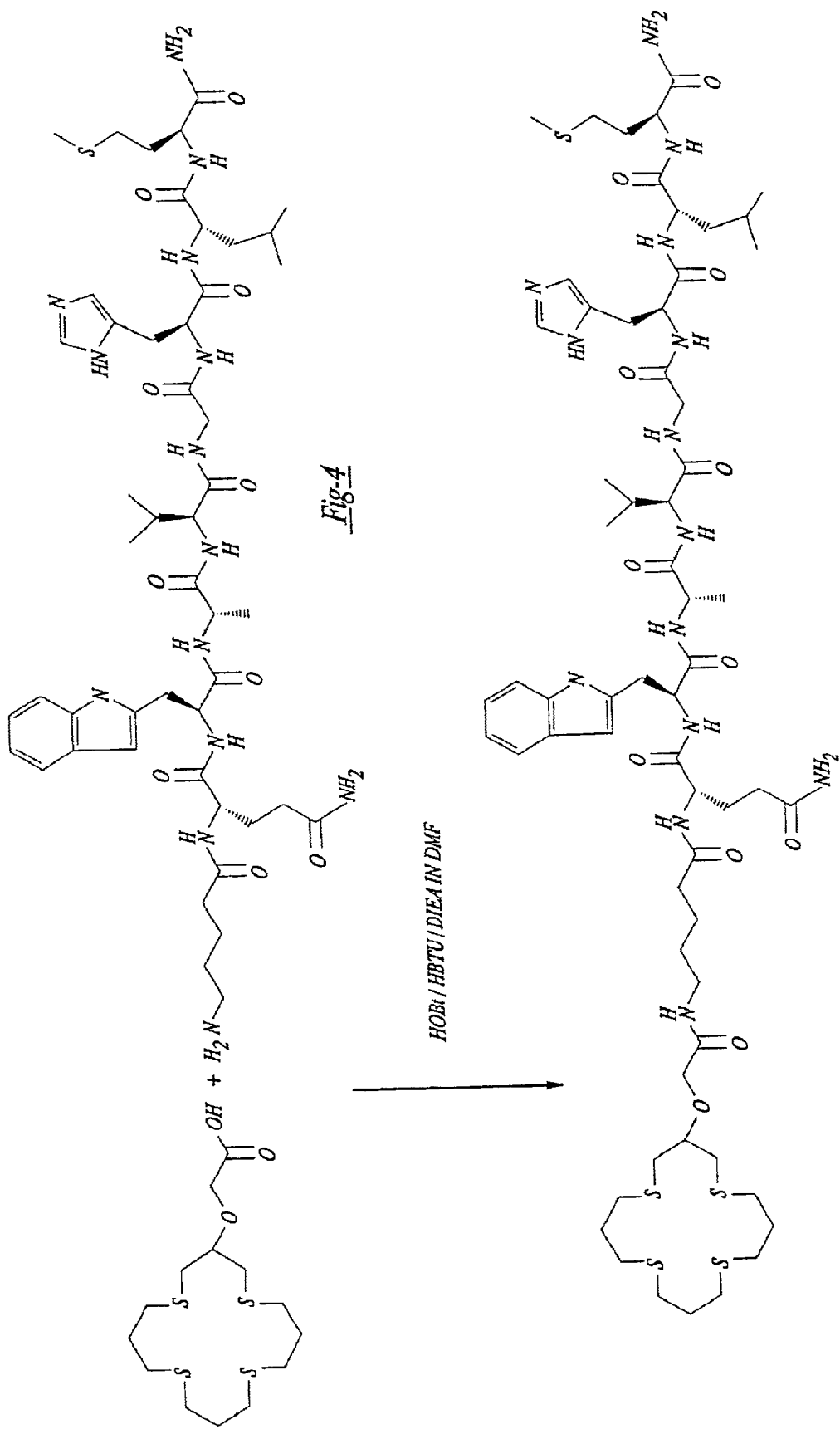
FIG. 4 illustrates a coupling reaction for coupling a metal chelate to a peptide.

The chelator backbones used in accordance with the present invention are commercially available or they could be made by methods similar to those outlined in the literature [Frizberg et al., 1995; Lister-James et al., 1997; Li et al., 1996b; Albert et al., 1991; Pollak et al., 1996; de Jong et al., 1997; Smith et al., 1997; Seifert et al., 1998]. Attachment of the spacer groups to functionalizable atoms appended to the ligand backbone can be performed by standard methods known to those skilled in the art. For example, the HOBt/HBTU activated —COOH group on 5-aminovaleric acid (5-AVA) was reacted with the N-terminal amine on Gln$^7$ to produce an amide linkage as shown in FIG. 3. Similarly, the —COOH group attached to the characterized [16]aneS$_4$ ligand was conjugated to the amine group on the hydrocarbon spacer (shown below) by reaction of the HOBt/HBTU activated carboxyl group appended to the [16]aneS$_4$ macrocycle with the terminal amine group on 5-AVA to form BBN-37 as shown in FIG. 4. Other standard conjugation reactors that produce covalent linkages with amine groups can also be used [Wilbur, 1992; Parker, 1990].

The chelating framework, conjugated via Trp$^8$, complexes the radiometals should form a 1:1 chelator to metal ratio. Since $^{99m}$Tc has a short half-life (6 hour) and is a diagnostic radionuclide, the method of forming the $^{99m}$Tc-BBN analogues should permit complexation (either directly or by transmetallation) of $^{99m}$Tc to the conjugated chelating framework in a one-step, high yield reaction (exemplified below in the Experimental Section).

In contrast, the longer half lives of the therapeutic radionuclides (e.g., $^{105}$Rh, $^{186/188}$Re, $^{153}$Sm, $^{166}$Ho, $^{90}$Y, or $^{99}$Au) permit formation of the corresponding radiolabeled BBN analogues by either a one step high yield complexation step or by preforming a $^{105}$Rh—, $^{186/188}$Re—, $^{153}$Sm, $^{166}$Ho, $^{90}$Y or $^{199}$Au chelate synthon followed by conjugation of the preformed complex to the N-terminal end of the BBN binding moiety. In all cases, the resulting specific activity of the final radiolabeled BBN derivative must be high (i.e., >1 Ci/μmole).

Re- and Tc-Conjugates

Re and Tc are both in row VIIB of the Periodic Table and they are chemical congeners. Thus, for the most part, the complexation chemistry of these two metals with ligand frameworks that exhibit high in vitro and in vivo stabilities are the same [Eckelman, 1995]. Many $^{99m}$Tc or $^{186/188}$Re complexes, which are employed to form stable radiometal complexes with peptides and proteins, chelate these metals in their +5 oxidation state [Lister-James et al., 1997]. This oxidation state makes it possible to selectively place $^{99m}$Tc- or $^{186/188}$Re into ligand frameworks already conjugated to the biomolecule, constructed from a variety of $^{99m}$Tc(V) and/or $^{186/188}$Re(V) weak chelates (e.g., $^{99m}$Tc-glucoheptonate, citrate, gluconate, etc.) [Eckelman, 1995; Lister-James et al., 1997; Pollak et al., 1996]. Tetradentate ligand frameworks have been shown to form well-defined, single chemical species in high specific activities when at least one thiol group or at least one hydroxymethylene phosphine group is present on the ligand backbone [Smith et al., 1997].

Ligands which form stable Tc(V) or Re(V) tetradentate complexes containing, but not limited to, amino N-atoms, amido-N-atoms, carboxy-O-atoms and thioether-S-atoms, are donor atoms that can also be present [Eckelman, 1995; Fritzberg et al., 1992; Parker, 1990; Frizberg et al., 1995; Pollak et al., 1996; Seifert et al., 1998]. Depending upon the mix of donor atoms (groups), the overall complex charge normally ranges from −1 to +1.

Incorporation of the metal within the conjugate can be achieved by various methods commonly known in the art of coordination chemistry. When the metal is technetium-99m, the following general procedure can be used to form a technetium complex. A peptide-chelator conjugate solution is formed by initially dissolving the conjugate in aqueous alcohol such as ethanol. The solution is then degassed to remove oxygen. When an —SH group is present in the peptide, the thiol protecting group are removed with a suitable reagent, for example with sodium hydroxide, and are then neutralized with an organic acid such as acetic acid (pH 6.0–6.5). In the labeling step, sodium pertechnetate obtained from a molybdenum generator is added to a solution of the conjugate with a sufficient amount of a reducing agent, such as stannous chloride, to reduce technetium and is then heated. The labeled conjugate can be separated from the contaminants $^{99m}TcO_4^-$ and colloidal $^{99m}TcO_2$ chromatographically, for example with a C-18 Sep Pak cartridge [Millipore Corporation, Waters Chromatography Division, 34 Maple Street, Milford, Mass. 01757].

In an alternative method, the labeling can be accomplished by a transchelation reaction. The technetium source is a solution of technetium complexed with labile ligands facilitating ligand exchange with the selected chelator. Examples of suitable ligands for transchelation includes tartrate, citrate, gluconate, and heptagluconate. It will be appreciated that the conjugate can be labeled using the techniques described above, or alternatively, the chelator itself may be labeled and subsequently coupled to the peptide to form the conjugate; a process referred to as the "prelabeled chelate" method.

When labeled with diagnostically and/or therapeutically useful metals, peptide-chelator conjugates or pharmaceutically acceptable salts, esters, amides, and prodrugs of the present invention can be used to treat and/or detect cancers, including tumors, by procedures established in the art of radiodiagnostics and radiotherapeutics. [Bushbaum, 1995; Fischman et al., 1993; Schubiger et al., 1996; Lowbertz et al., 1994; Krenning et al., 1994]. A conjugate labeled with a radionuclide metal, such as technetium-99m, can be administered to a mammal, including human patients or subjects, by intravenous or intraperitoneal injection in a pharmaceutically acceptable carrier and/or solution such as salt solutions like isotonic saline. The amount of labeled conjugate appropriate for administration is dependent upon the distribution profile of the chosen conjugate in the sense that a rapidly cleared conjugate may be administered in higher doses than one that clears less rapidly. Unit doses acceptable for Tc-99m imaging radiopharmaceuticals inflammation are in the range of about 5–40 mCi for a 70 kg individual. In vivo distribution and localization can be tracked by standard scintigraphic techniques at an appropriate time subsequent to administration; typically between thirty minutes and 180 minutes depending upon the rate of accumulation at the target site with respect to the rate of clearance at non-target tissue.

The compounds of the present invention can be administered to a patient alone or as part of a composition that contains other components such as excipients, diluents, and carriers, all of which are well-known in the art. The compounds can be administered to patients either intravenously or intraperitoneally.

There are numerous advantages associated with the present invention. The compounds made in accordance with the present invention forms a stable, well-defined $^{99m}Tc$ or $^{186/188}Re$ conjugate analogues of BBN agonists. Similar BBN against analogues can also be made by using appropriate chelator frameworks for the respective radiometals, to form stable-well-defined products labeled with $^{153}Sm$, $^{90}Y$, $^{166}Ho$, $^{105}Rh$ or $^{199}Au$. The radiolabeled BBN agonist conjugates selectively bind to neoplastic cells expressing GRP receptors become internalized and are retained in the tumor cells for extended time periods. Incorporating the spacer group between the metal chelator and the BBN agonist binding moiety maximizes the uptake and retention of the radioactive metal inside of the neoplasts or cancer cells. The radioactive material that does not reach (i.e., does not bind) the cancer cells is preferentially excreted efficiently into the urine with minimal radiometal retention in the kidneys.

The following examples are presented to illustrate specific embodiments and demonstrate the utility of the present invention.

Experimental Section

EXAMPLE I

Synthesis and In Vitro Binding Assessment of Synthetic BBN Analogues Employing Hydrocarbon Chain Spacers A. Synthesis:

Many BBN analogues were synthesized by Solid Phase Peptide Synthesis (SPPS). Each peptide was prepared by SPPS using an Applied Biosystems Model 432A peptide synthesizer. After cleavage of each BBN analogue from the resin using Trifluoracetic acid (TFA), the peptides were purified by $C_{18}$ reversed-phase HPLC using a Vydac HS54 column and $CH_3CN/H_2O$ containing 0.1% TFA as the mobile phase. After collection of the fraction containing the desired BBN peptide (approx. 80–90% yield in most cases), the solvent was evaporated. The identity of each BBN peptide was confirmed by FAB-mass spectrometry, Department of Chemistry—Washington University, St. Louis, Mo.

Figure 5:
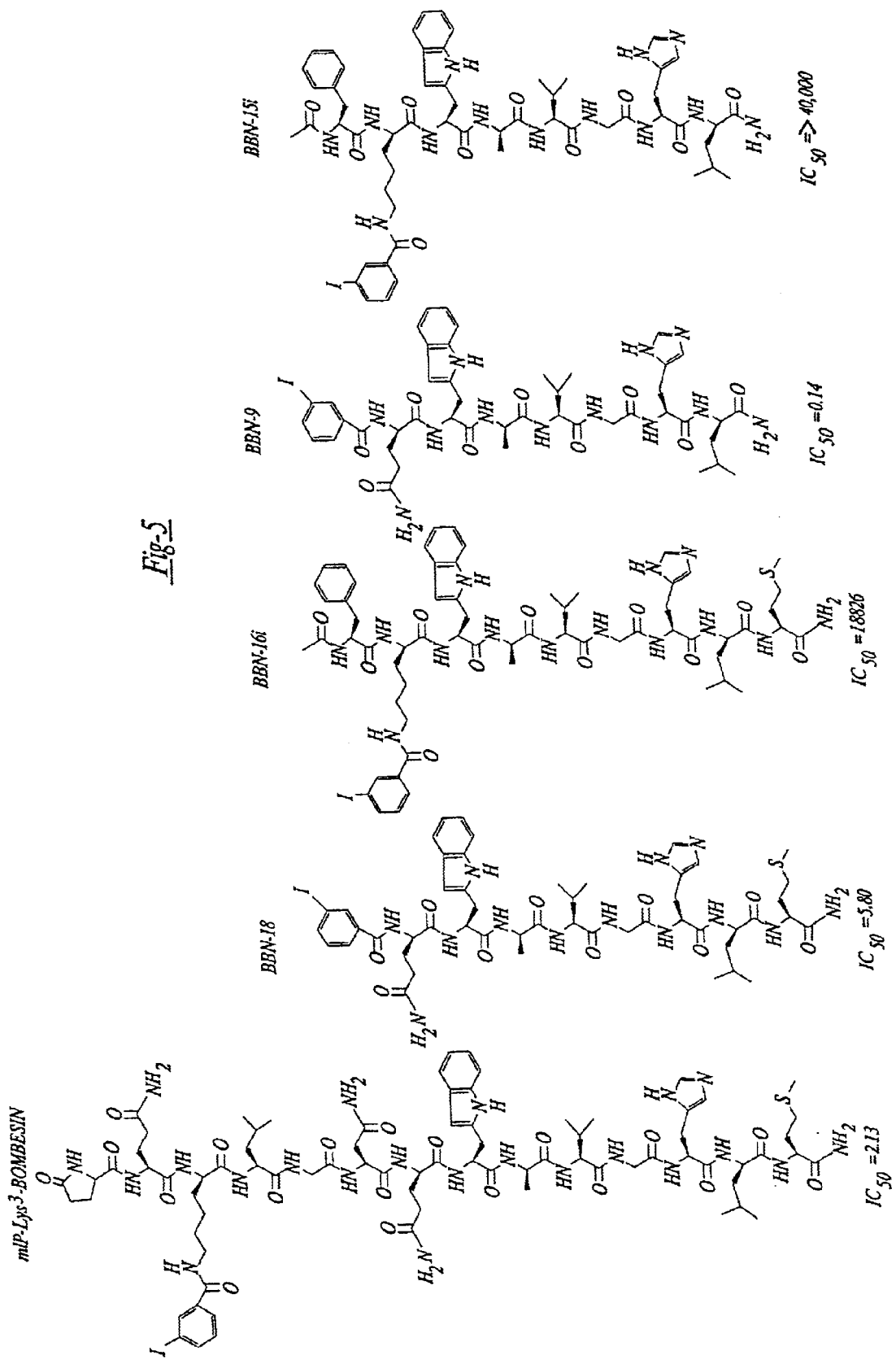
FIG. 5 illustrates several iodinated bombesin analogues including their $IC_{50}$'s.
Figure 6A:
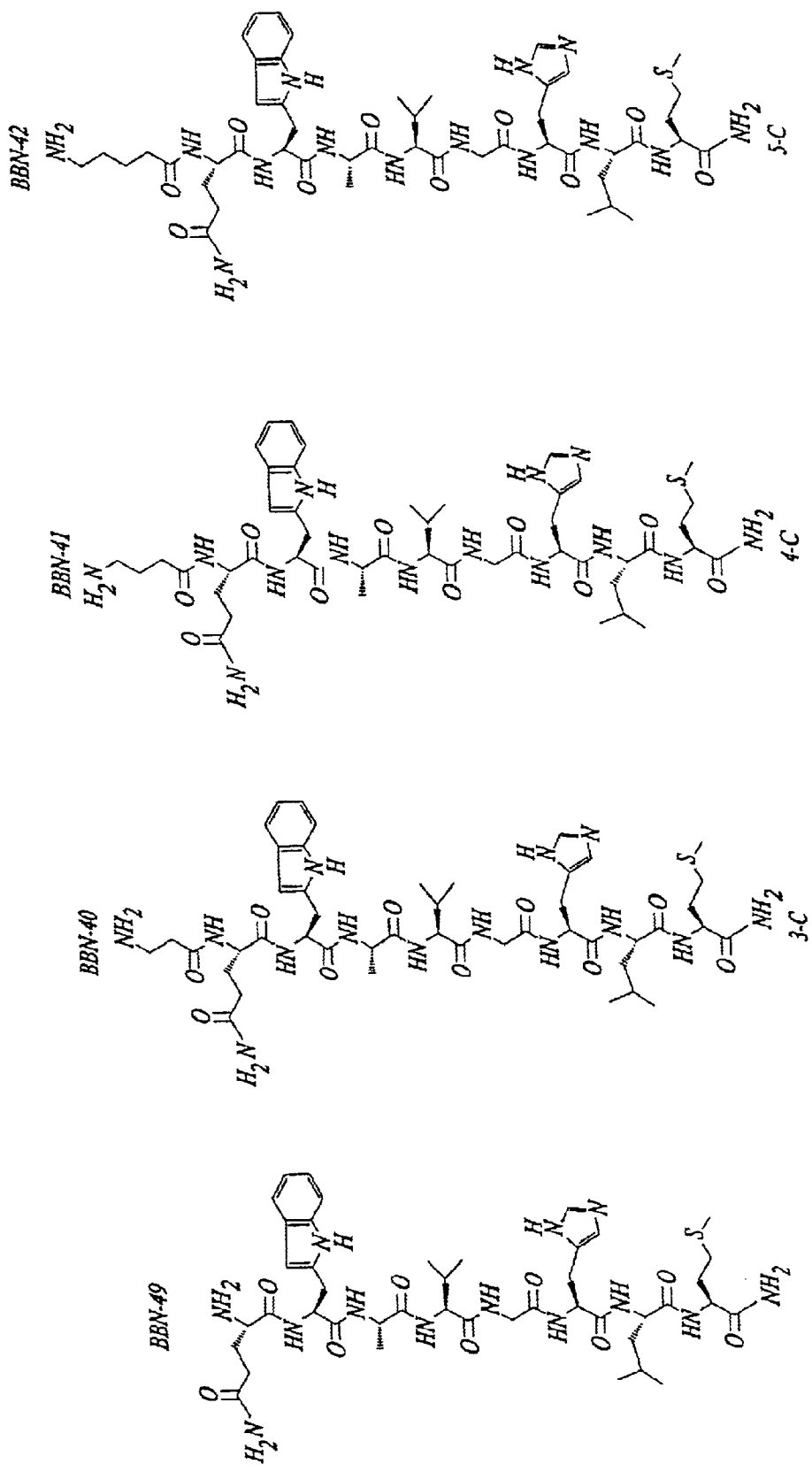
FIG. 6 illustrates several tethered bombesin analogues.
Figure 6B:
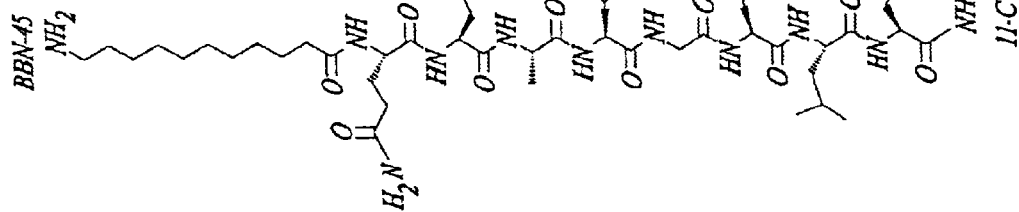
Figure 6B:
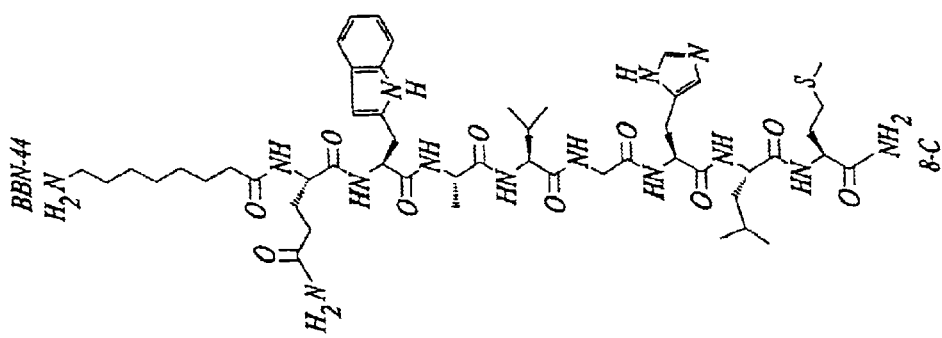
Figure 6B:
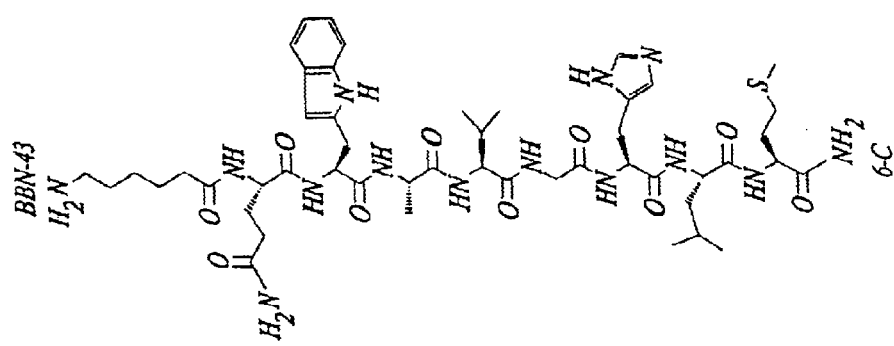

Various amino acid sequences (in some cases including different chemical moieties) were conjugated to the N-terminal end of the BBN binding region (i.e., to BBN-8 or Trp$^8$). BBN analogue numbers 9, 15, 15i, 16, 16i and 18 were synthesized as examples of N-terminal modified peptides as shown in FIG. 5.

Various tethered N-terminal (via Trp$^8$) BBN analogues were also synthesized by SPPS as exemplified by BBN-40, BBN-41, BBN-42, BBN-43, BBN-44, BBN-45, and BBN-49 as shown in FIG. 6. In these particular tethered peptides, a Glu residue was attached to Trp$^8$ followed by attachment of FmOC protected terminal amine groups separated from a —COOH group by 3-, 4-, 5-, 6-, 8- and 11-carbon chain (CH) spacers (FIG. 6). These FmOC protected acids were added as the terminal step during the SPPS cycle. As described previously, each of the BBN analogues was purified by reversed-phase HPLC and characterized by high resolution Mass Spectroscopy. Peptide 49 employed only glutamine as the spacer group.

Figure 7:
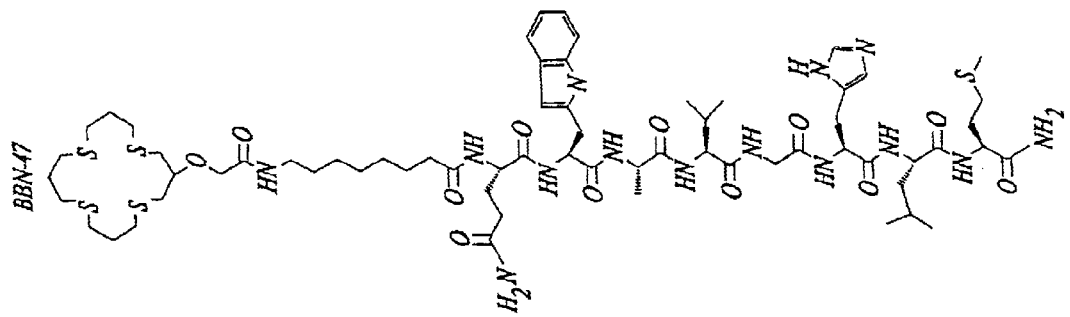
FIG. 7 illustrates several [16]aneS$_4$ bombesin analogues.
Figure 7:
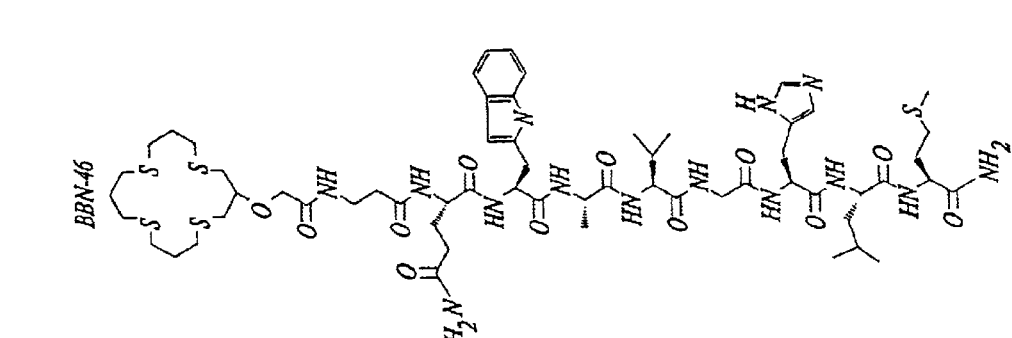
Figure 7:
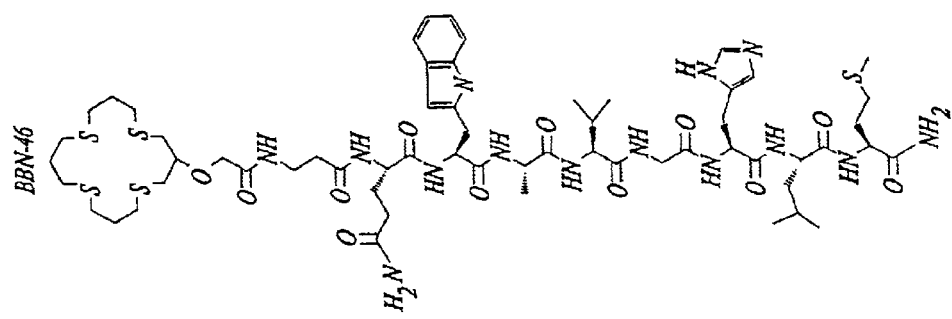
Figure 7:
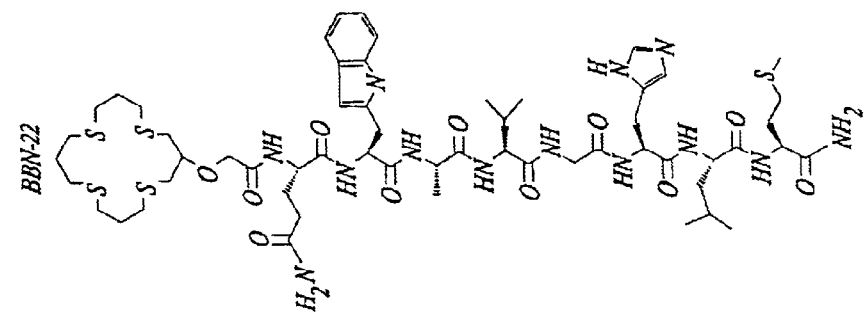

The [16]aneS$_4$ macrocyclic ligand was conjugated to selected tethered BBN analogues shown in FIG. 6. The —OCH$_2$COOH group on the [16]aneS$_4$ macrocycle derivative was activated via HOBt/HBTU so that it efficiently formed an amide bond with the terminal NH$_2$ group on the spacer side arm (following deprotection). The corresponding [16]aneS$_4$ tethered BBN derivatives were produced and examples of 4 of these derivatives (i.e., BBN-22, -37, -46 and -47) are shown in FIG. 7. As previously described, each [16]aneS$_4$ BBN derivative was purified by reversed phase HPLC and characterized by FAB Mass Spectroscopy.

B. In Vitro Binding Affinities

The binding affinities of the synthetic BBN derivatives were assessed for GRP receptors on Swiss 3T3 cells and, in some cases, on a variety of human cancer cell lines, that express GRP receptors. The IC$_{50}$'s of each derivative was determined relative to (i.e., in competition with) $^{125}$I-Tyr$^4$-BBN (the K$_d$ for $^{125}$I-Tyr$^4$-BBN for GRP receptors in Swiss 3T3 cells is reported to be 1.6±0.4 nM) [Zueht et al., 1991]. The cell binding assay methods used to measure the IC$_{50}$'s is standard and was used by techniques previously reported [Jensen et al., 1993; Cai et al., 1994; Cai et al., 1992]. The methods used for determining IC$_{50}$'s with all GRP receptor binding of GRP receptors on all cell lines was similar. The specific method used to measure $IC_{50}$'s on Swiss 3T3 cells is briefly described as follows:

Swiss 3T3 mouse fibroblasts are grown to confluence in 48 well microtiter plates. An incubation media was prepared consisting of HEPES (11.916 g/l), NaCl (7.598 g/l), KCl (0.574 g/l), $MgCl_2$ (1.106 g/l), EGTA (0.380 g/l), BSA (5.0 g/l), chymostatin (0.002 g/l), soybean trypsin inhibitor (0.200 g/l), and bacitracin (0.050 g/l). The growth media was removed, the cells were washed twice with incubation media, and incubation media was returned to the cells. $^{125}I$-$Tyr^4$-BBN (0.01 uCi) was added to each well in the presence of increasing concentrations of the appropriate competitive peptide. Typical concentrations of displacing peptide ranged from $10^{-12}$ to $10^{-5}$ moles of displacing ligand per well. The cells were incubated at 37° C. for forty minutes in a 95% $O_2$/5% $CO_2$ humidified environment. At forty minutes post initiation of the incubation, the medium was discarded, and the cells were washed twice with cold incubation media. The cells were harvested from the wells following incubation in a trypsin/EDTA solution for five minutes at 37° C. Subsequently, the radioactivity, per well, was determined and the maximum % total uptake of the radiolabeled peptide was determined and normalized to 100%.

C. Results of Binding Affinity Measurements

Figure 8:
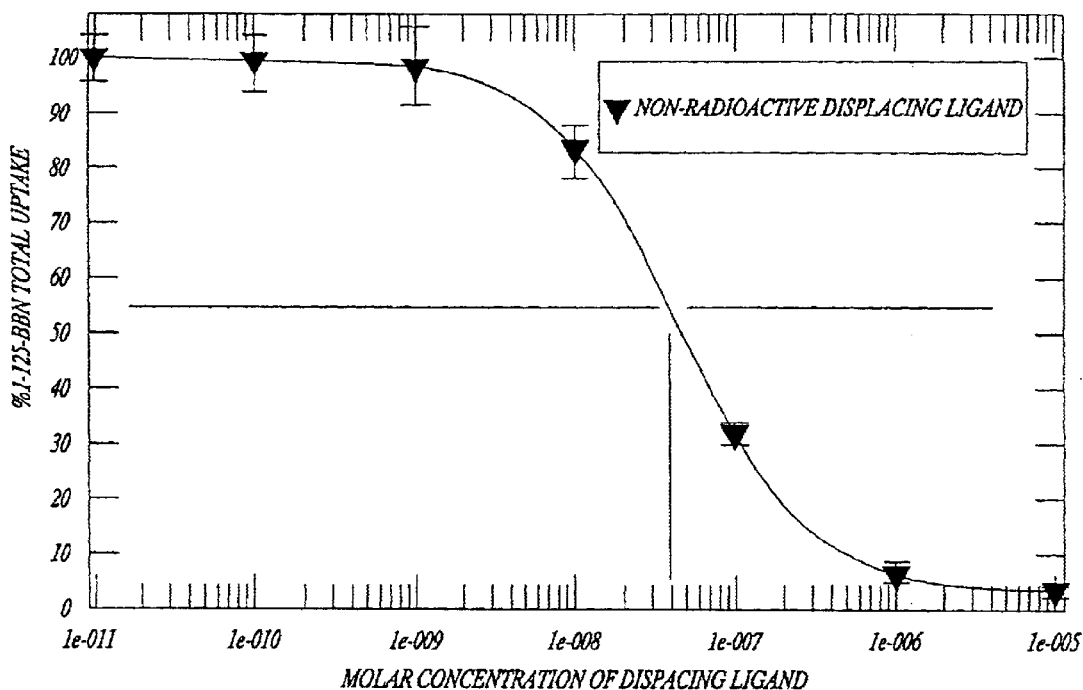
FIG. 8 is a graph illustrating $IC_{50}$ analysis wherein %-I-125-BBN total uptake versus molar concentration of displacing ligand is shown.

The $IC_{50}$ values measured for the BBN derivatives synthesized in accordance with this invention showed that appending a peptide side chain and other moieties via the N-terminal BBN-8 residue (i.e., $Trp^8$) produced widely varying $IC_{50}$ values. For example, see $IC_{50}$ values shown for BBN 11, 15i, 16i, and 18 in FIGS. 5 and 8. The observations are consistent with previous reports showing highly variable $IC_{50}$ values when derivatizing BBN(8–13) or BBN(8–14) with a predominantly short chain of amino acid residues [Hoffken, 1994]. In contrast, when a hydrocarbon spacer of 3- to 11-carbons was appended between BBN(7–14) and the [16]ane$S_4$ macrocycle, the $IC_{50}$'s were found to be surprisingly relatively constant and in the 1–5 nM range (i.e., see $IC_{50}$ values for BBN-22, -37, -46 and -47 as shown in FIG. 7). These data suggest that using relatively simple spacer groups to extend ligands some distance from the BBN binding region [e.g., BBN(8–14)] can produce derivatives that maintain binding affinities in the 1–5 nmolar range.

D. Cell Binding Studies

Figure 9:
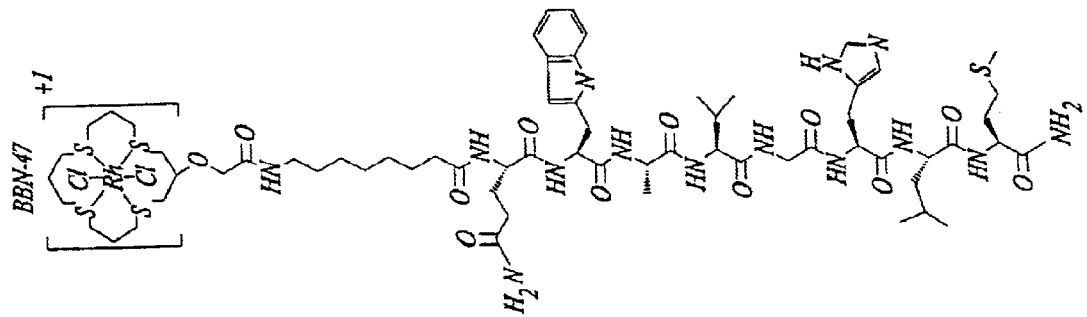
FIG. 9 illustrates several Rhodium-[16]aneS$_4$ bombesin analogues.
Figure 9:
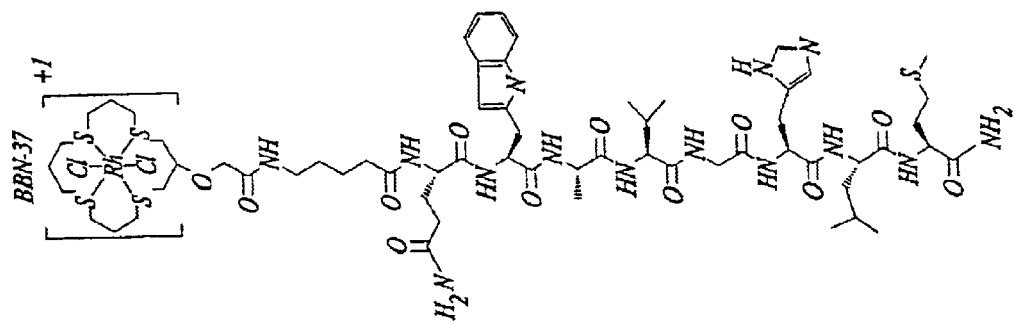
Figure 9:
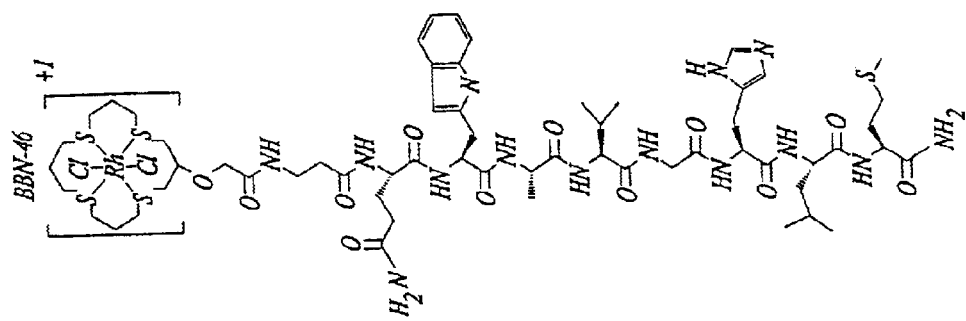
Figure 9:
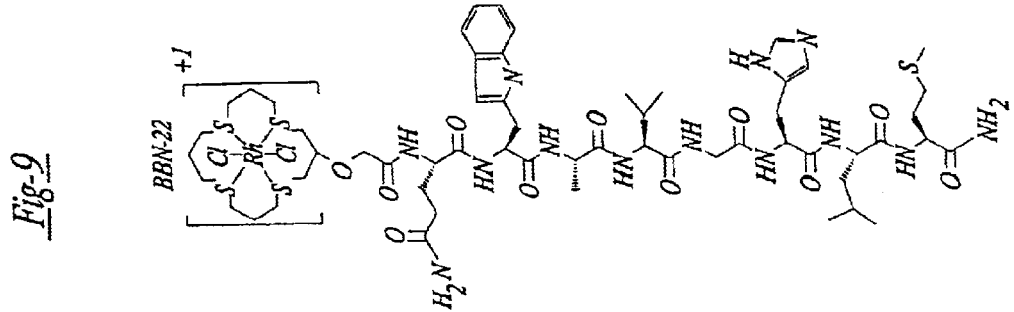

Results illustrated in FIG. 9 show that when the $RhCl_2$-[16]ane$S_4$ complex separated from $Trp^8$ by only a glutamine ($Glu^7$), the $IC_{50}$ of this conjugate (i.e., Rh-BBN-22) was 37.5 nM. However, when a five (5) carbon spacer or an eight (8) carbon spacer was present (i.e., Rh-BBN-37 and Rh-BBN-47), the $IC_{50}$'s remained below 5 nM as shown in FIG. 9. These data demonstrate that a straight chain spacer (along with $glu^7$) to move the +1 charged Rh—$S_4$-chelate away from the BBN binding region will result in a metallated BBN analogue with sufficiently high binding affinities to GRP receptors for in vivo tumor targeting applications.

E. $^{105}$Radiolabeled BBN Analogues

Figure 10A:
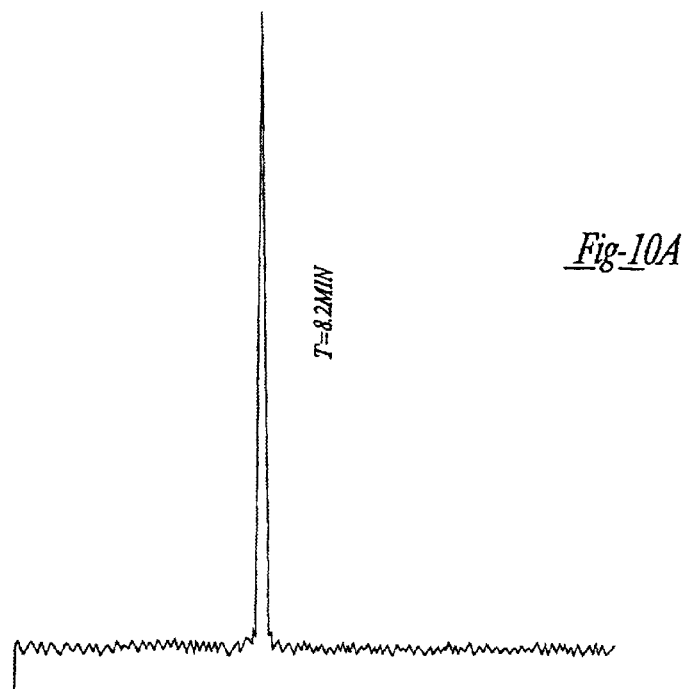
FIG. 10 illustrates an HPLC chromatogram of Rhodium-BBN-37 wherein (A) illustrates $^{105}RhCl_2$-BBN-37 and (B) illustrates $RhCl_2$-BBN-37.
Figure 10B:
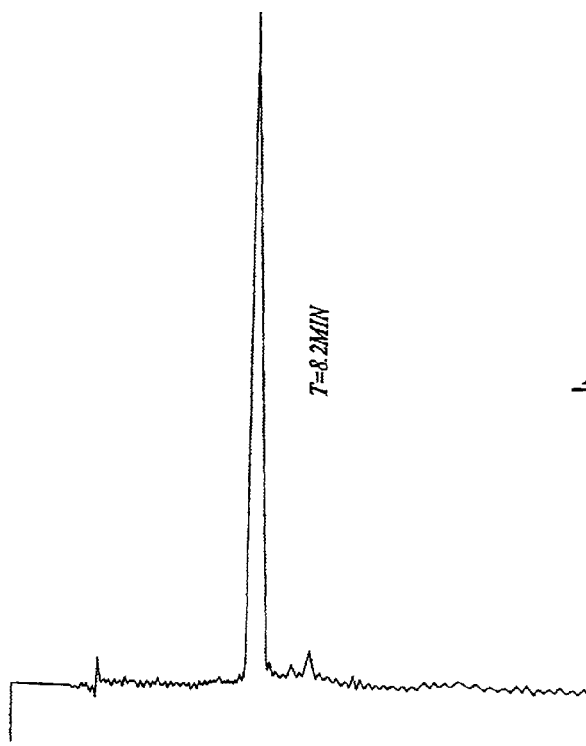

The $^{105}$Rh conjugates of BBN-22, BBN-37, BBN-46 and BBN-47 were synthesized using a $^{105}$Rh-chloride reagent from the Missouri University Research Reactor (MURR). This reagent was obtained as $^{105}$Rh-chloride, a no-carrier-added (NCA) product, in 0.1–1M HCl. The pH of this reagent was adjusted to 4–5 using 0.1–1.0 M NaOH dropwise and it was added to approximately 0.1 mg of the [16]ane$S_4$-conjugated BBN derivatives in 0.9% aqueous NaCl and 10% ethanol. After the sample was heated at 80° C. for one hour, the $^{105}$Rh-BBN analogues were purified using HPLC. In each case, a NCA or high specific activity product was obtained since the non-metallated $S_4$-BBN conjugates eluted at a retention time well after the $^{105}$Rh-BBN conjugates eluted. For example, the retention time of $^{105}$Rh-BBN-37 was 7.1 min while BBN-37 eluted at 10.5 min from a C-18-reversed phase column eluted with $CH_3CN/H_2O$ containing 0.1% TFA as shown in FIGS. 10A–B.

EXAMPLE II

Retention of $^{105}$Rh-BBN Analogues in Cancer Cells

Once the radiometal has been specifically "delivered" to cancer cells (e.g., employing the BBN binding moiety that specifically targets GRP receptors on the cell surface), it is necessary that a large percentage of the "delivered" radioactive atoms remain associated with the cells for a period time of hours or longer to make an effective radiopharmaceutical for effectively treating cancer. One way to achieve this association is to internalize the radiolabeled BBN conjugates within the cancer cell after binding to cell surface GRP receptors.

Figure 11:
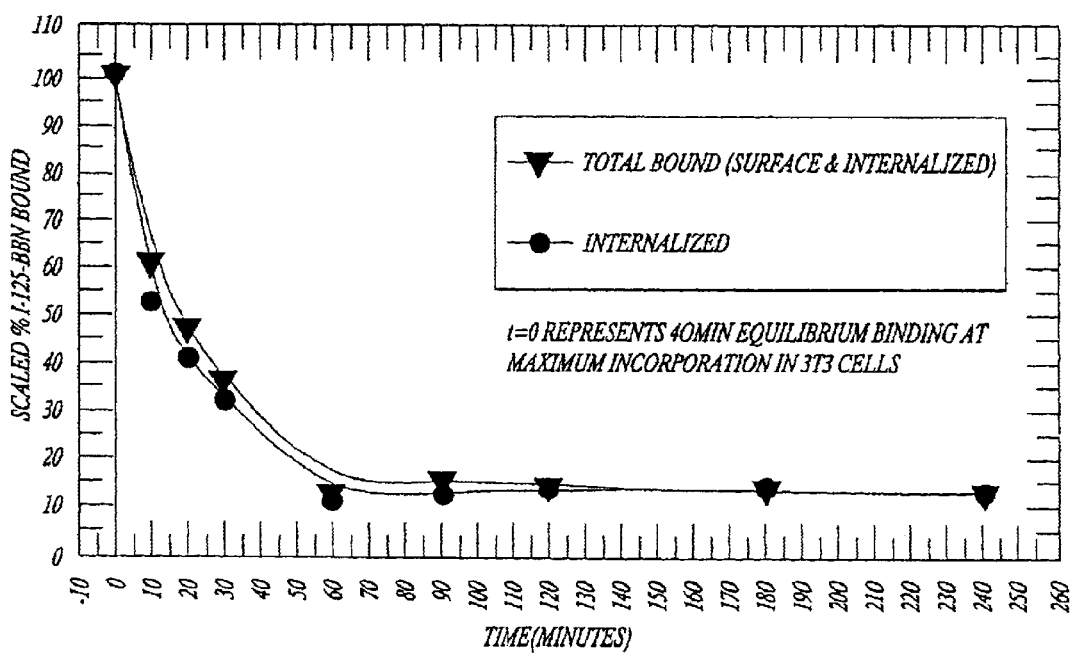
FIG. 11 is a graph illustrating $^{125}I$-Tyr$^4$-bombesin internalization efflux from Swiss 3T3 cells.

In the past, all of the work with synthetic-BBN analogues for treatment of cancers focused on synthesizing and evaluating antagonists [Davis et al., 1992; Hoffken, 1994; Moody et al., 1996; Coy et al., 1988; Cai et al., 1994; Moody et al., 1995; Leban et al., 1994; Cai et al., 1992]. After evaluating synthetic BBN analogues that would be predicted to be either agonists or antagonists, applicants found that derivatives of BBN(8–14) (i.e., those with the methionine or amidated methionine at BBN-14) are rapidly internalized (i.e., in less than two minutes) after binding to the cell surface GRP receptors. Several radiolabeled BBN(8–14) analogues that were studied to determine their internalization and intracellular trapping efficiencies were radioiodinated (i.e., 125I) derivatives. The results of these studies demonstrated that despite rapid internalization after $^{125}$I-labeled BBN analogue binding to GRP receptors in Swiss 3T3 cells, the $^{125}$I was rapidly expelled from the cells [Hoffman et al., 1997] as shown in FIG. 11. Thus, these $^{125}$I-BBN derivatives were not suitable for further development.

In contrast, the $^{105}$Rh-BBN(8–14) derivatives that bind to GRP receptors are not only rapidly internalized, but there is a large percentage of the $^{105}$Rh activity that remains trapped within the cells for hours (and in some cell lines >twenty four hours). This observation indicates that these radiometallated BBN derivatives have real utility as radiopharmaceuticals for in vivo targeting of neoplasms expressing GRP receptors.

Experiments designed to determine the fraction of a radiotracer internalized within cells were performed by adding excess 125I- or $^{105}$Rh-BBN derivatives to the cell incubation medium. After establishment of equilibrium after a forty minute incubation, the media surrounding the cells was removed and the cells were washed with fresh media containing no radioactivity. After washing, the quantity of radioactivity associated with the cells was determined (i.e., total counts per min (TCPM) of $^{125}$I or $^{105}$Rh associated with the cells). The cells were then incubated in a 0.2M acetic acid solution (pH 2.5) which caused the surface proteins (incl., GRP receptors) to denature and release all surface bound radioactive materials. After removing this buffer and washing, the cells were counted again. The counts per minute (c.p.m.) associated with the cells at that point were only related to the $^{125}$I or $^{105}$Rh that remained trapped inside of the cells.

Figure 12:
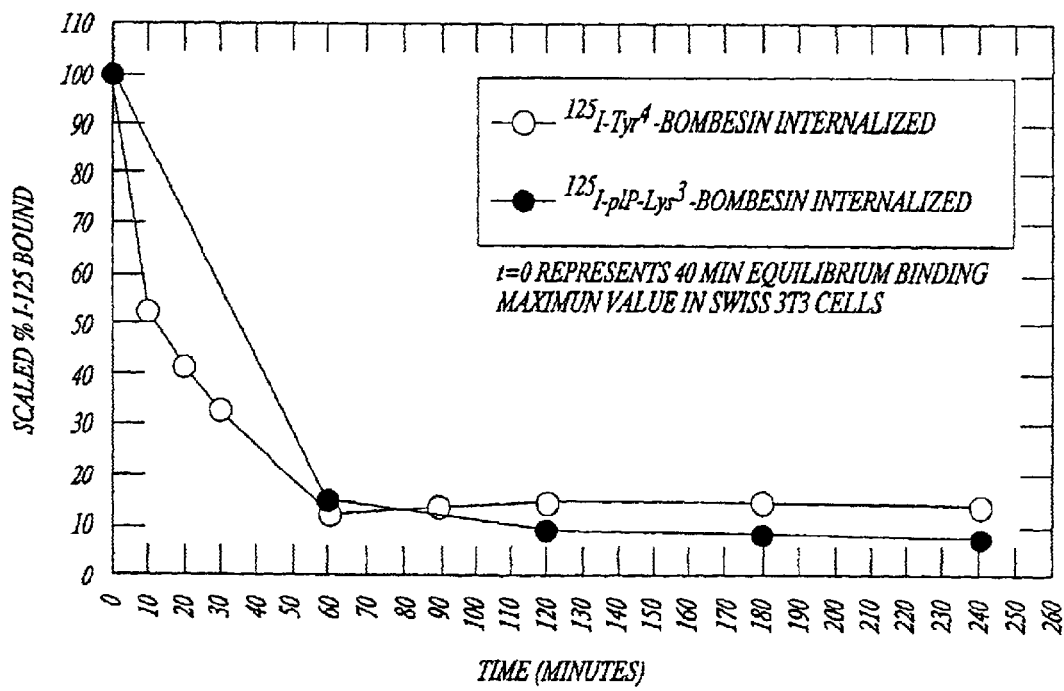
FIG. 12 illustrates I-125 bombesin internalization efflux in I-125 free buffer wherein $^{125}I$-Tyr$^4$-BBN vs. $^{125}I$-Lys$^3$-BBN efflux from Swiss 3T3 cells is shown.

To determine intracellular retention, a similar method was employed. However, after washing the cells with fresh (non-radioactive) incubation media, the cells were incubated in the fresh media at different time periods after washing away all extracellular $^{125}$I- or $^{105}$Rh-BBN analogues. After each time period, the methods used to determine TOTAL c.p.m. and intracellular c.p.m. after washing with a 0.2M acetic acid solution at pH 2.5 were the same as described above and the percent $^{125}$I or $^{105}$Rh remaining trapped inside of the cells was calculated. FIG. 12 is a graph of results of efflux experiments using Swiss 3T3 cells with $^{125}$I-Lys$^3$-BBN. The results show that there is rapid efflux of the 125I from inside of these cells with less than 50% retained at fifteen minutes and by sixty minutes, less than 20% remained as shown in FIG. 12.

Figure 13:
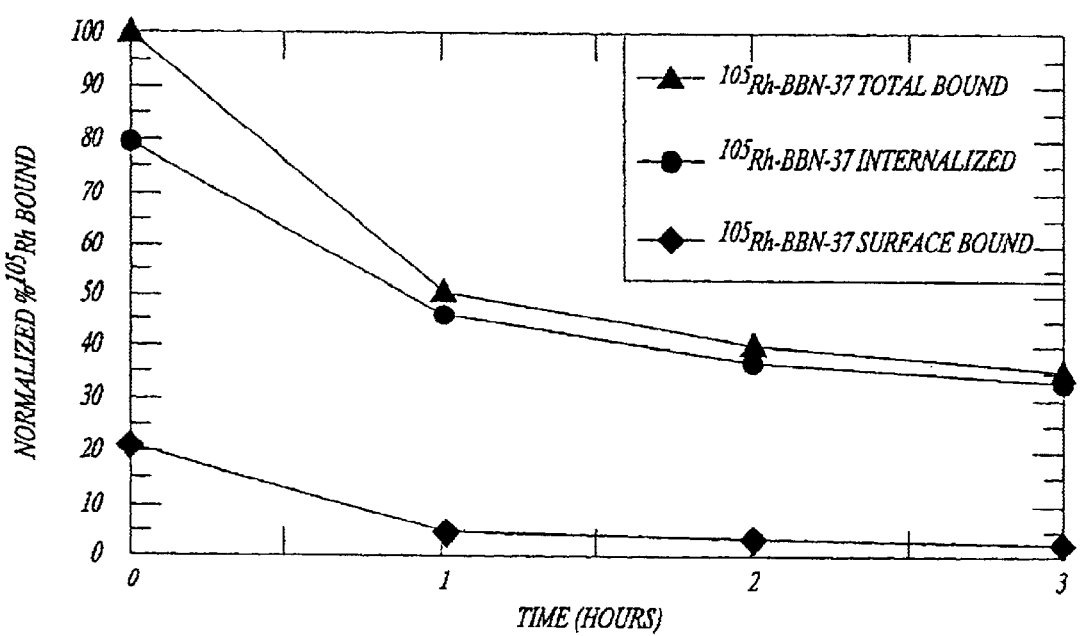
FIG. 13 is a graph illustrating the efflux of $^{105}Rh$-BBN-37 from Swiss 3T3 cells.

In contrast, studies with all of the $^{105}$Rh-[16]aneS$_4$-BBN agonist derivatives that are internalized inside of the cells showed substantial intracellular retention of $^{105}$Rh by the GRP receptor expressing cells. For example, results of studies using $^{105}$Rh-BBN-37 (see FIG. 9) in conjunction with Swiss 3T3 cells showed that approximately 50% of the $^{105}$Rh activity remains associated with the cells at sixty minutes post-washing and approximately 30% of $^{105}$Rh remained inside of the cells after four hours as shown in FIG. 13. Note that at least 5% of the $^{105}$Rh is surface bound at ≧sixty minutes.

Figure 14:
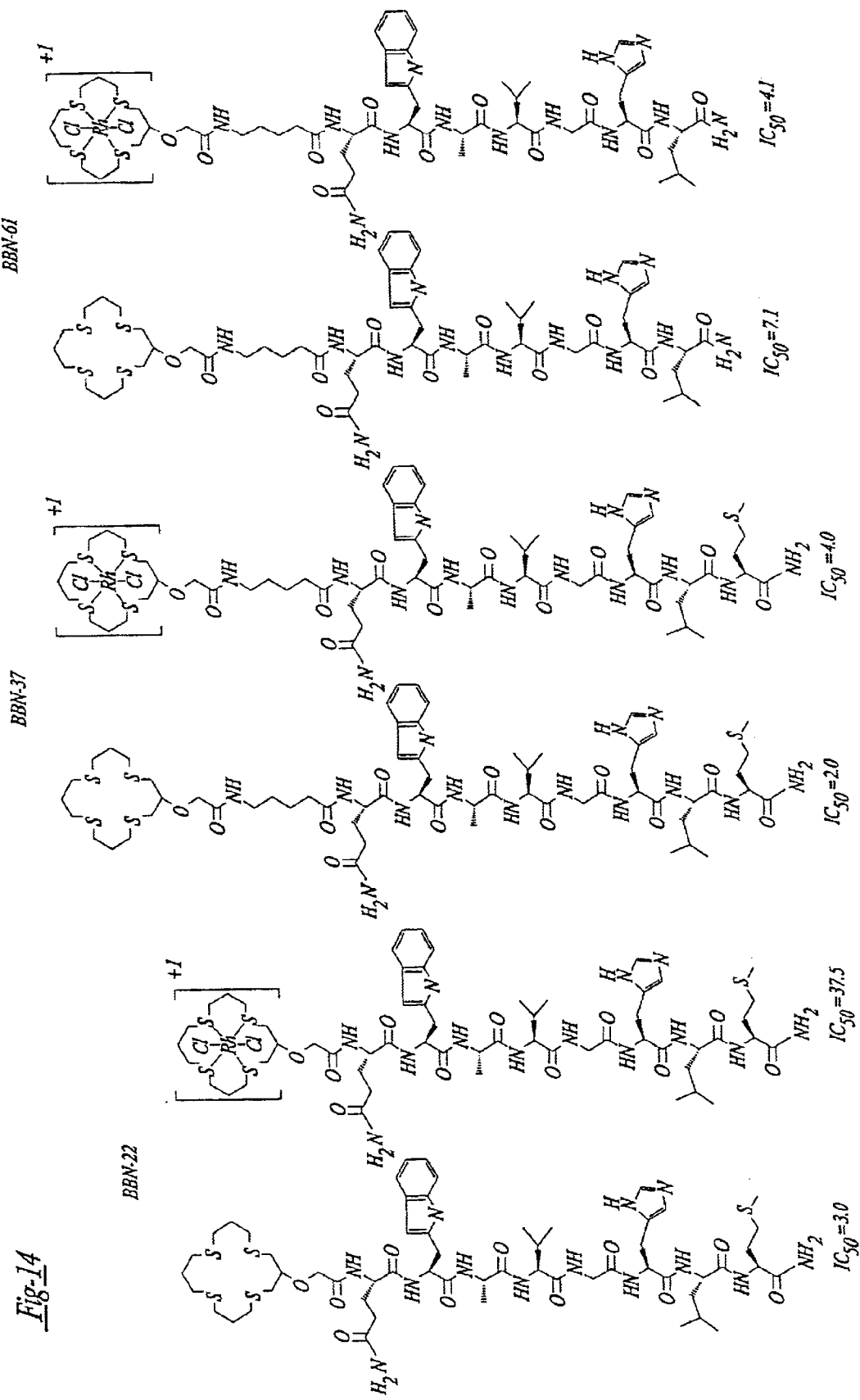
FIG. 14 illustrates several $^{105}$Rhodium bombesin analogues including their $IC_{50}$'s.
Figure 15:
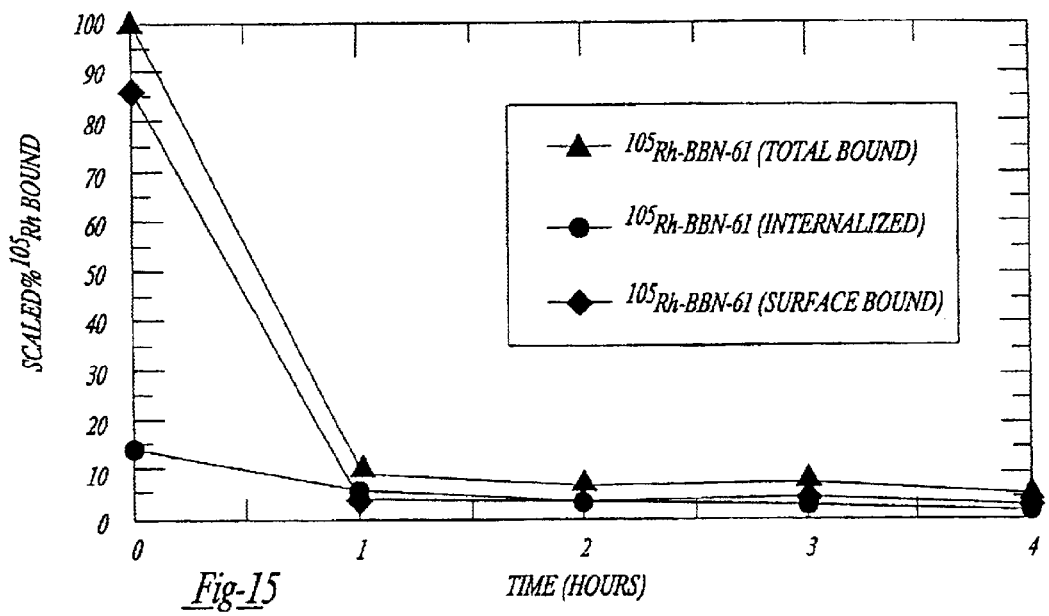
FIG. 15 is a graph illustrating $^{105}Rh$-BBN-61 efflux from Swiss 3T3 cells.
Figure 16:
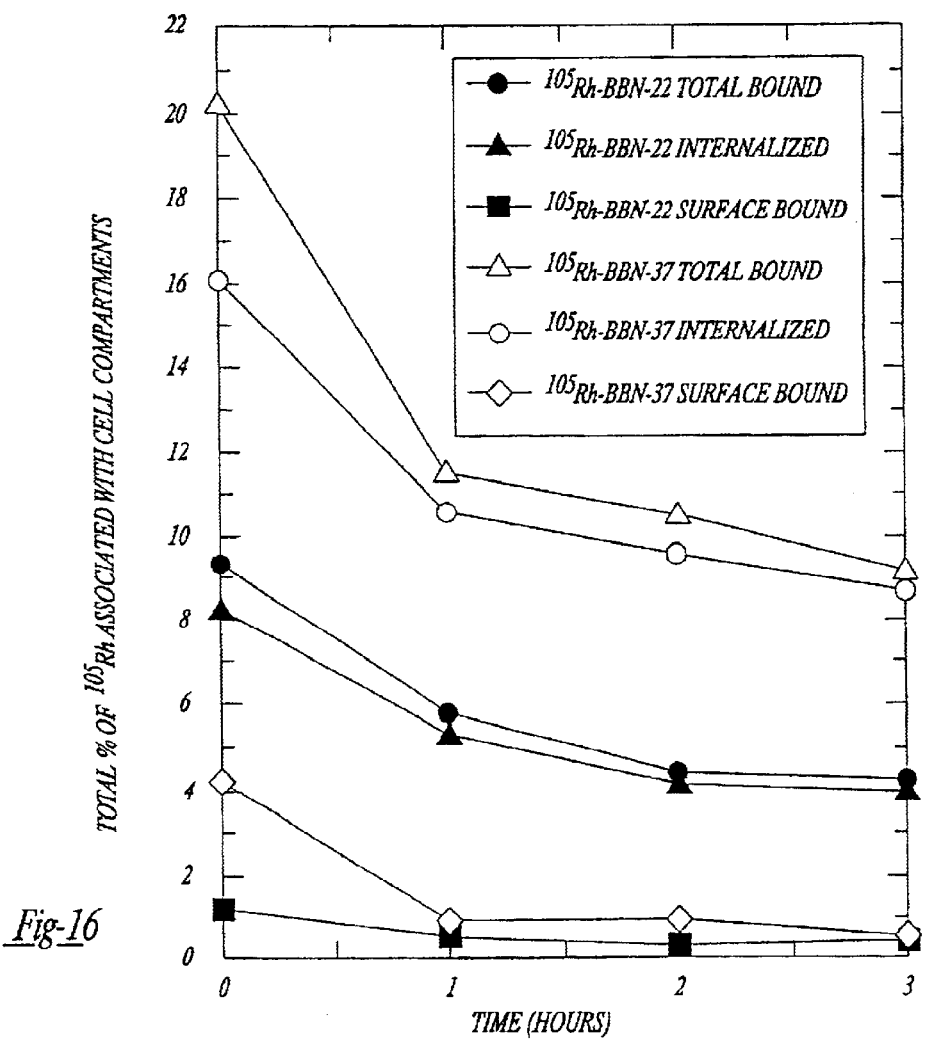
FIG. 16 is a graph illustrating the efflux of $^{105}Rh$-BBN-22 vs. $^{105}Rh$-BBN-37 from Swiss 3T3 cells.
Figure 17A:
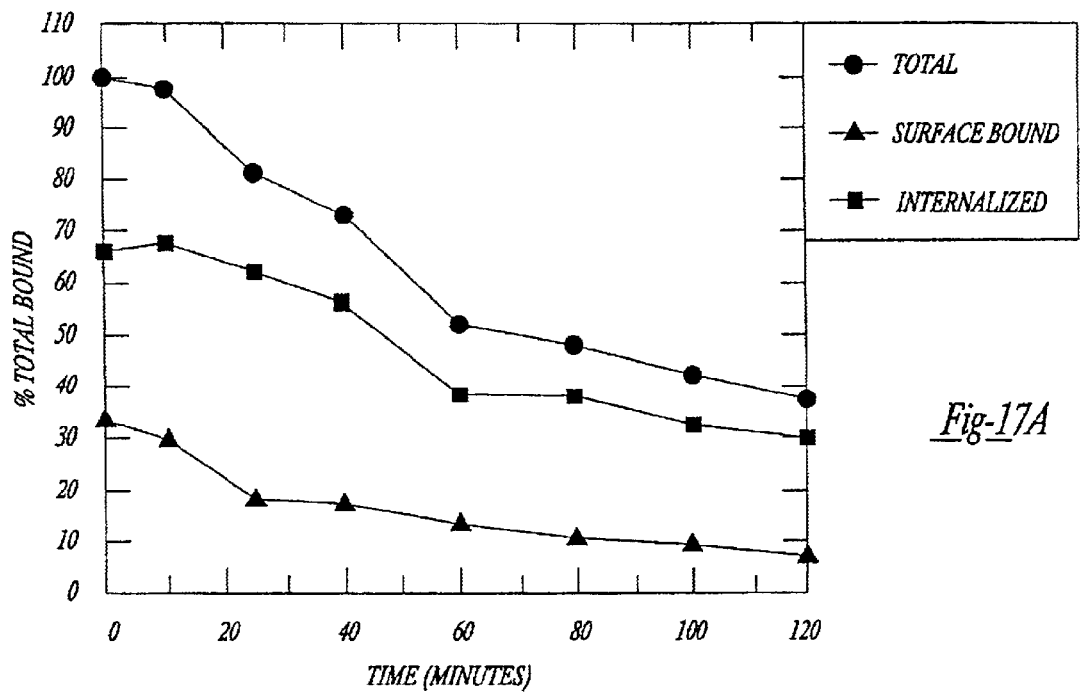
FIG. 17 are graphs illustrating Pancreatic CA cell binding wherein (A) illustrates the efflux $^{125}I$-Tyr$^4$-BBN from CF PAC1 cells and (B) illustrates the efflux of $^{105}Rh$-BBN-37 from CF PAC1 cells.
Figure 17B:
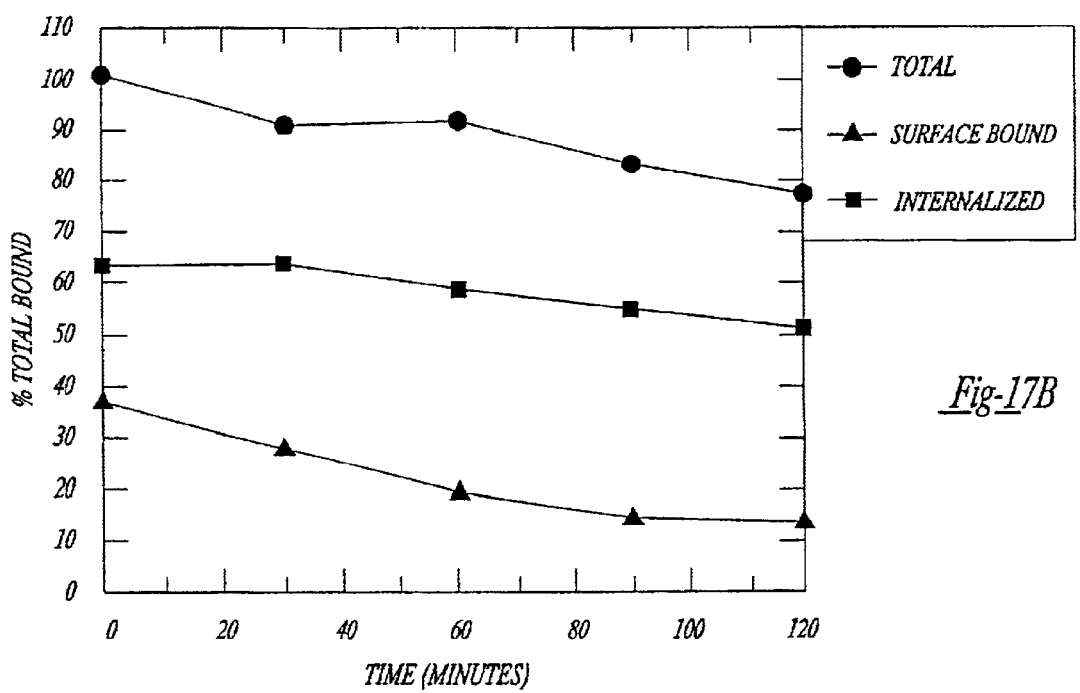
Figure 18A:
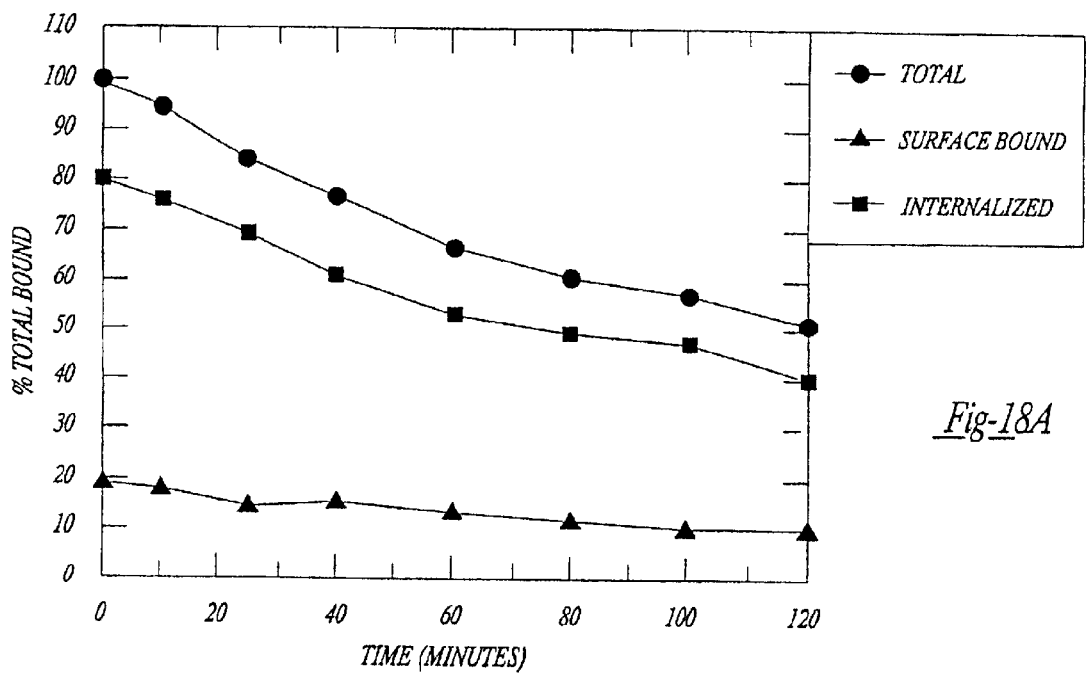
FIG. 18 are graphs illustrating Prostate CA cell binding wherein (A) illustrates the efflux of $^{125}I$-Tyr$^4$-BBN from PC-3 cells and (B) illustrates the efflux of $^{105}Rh$-BBN-37 from PC-3 cells.
Figure 18B:
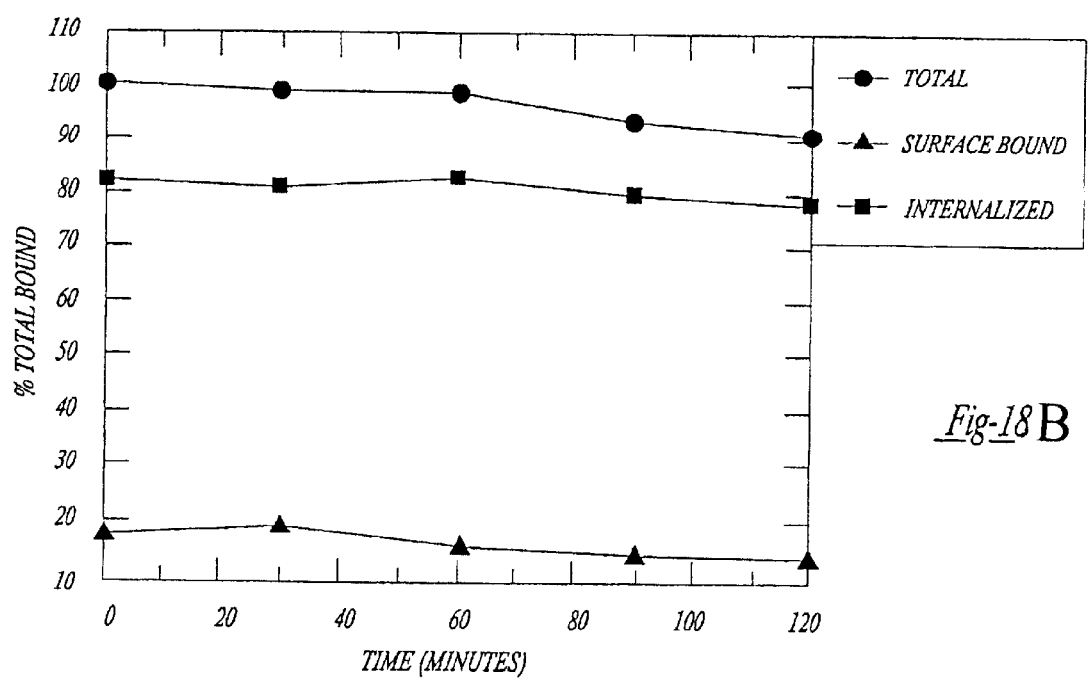

The $^{105}$Rh-BBN derivatives shown in FIG. 9 all have an amidated methionine at position BBN-14 and are expected to be agonists [Jensen et al., 1993]. Therefore, they would be predicted to rapidly internalize after binding to GRP receptors on the cell surface [Reile et al., 1994; Bjisterbosch et al., 1995; Smythe et al., 1991], which was confirmed by applicants' data. Referring to FIG. 14, $^{105}$Rh-BBN-61, a BBN analogue with no amino acid at position BBN-14 (i.e., a $^{105}$Rh-BBN(8–13) derivative), was synthesized and studied. This BBN analogue has a high bonding affinity (i.e., IC$_{50}$= 30 nM). This type of derivative is expected to be an antagonist and as such will not internalize [Jensen et al., 1993; Smythe et al., 1991]. Results of efflux studies with $^{105}$Rh-BBN-61 using Swiss 3T3 cells showed that immediately following washing with fresh incubation buffer (i.e., t=0), essentially all of the $^{105}$Rh associated with these cells is on the cell surface, as expected. Furthermore, after only one hour of incubation, less than 10% remained associated with these cells in any fashion (see FIGS. 15 and 16). These data indicate that $^{105}$Rh-antagonists with structures similar to the $^{105}$Rh-BBN agonists (i.e., those shown in FIG. 9) are not good candidates for development of radiopharmaceuticals since they are neither trapped in nor on the GRP receptor expressing cells to nearly the same extent as the radiometallated BBN agonists.

EXAMPLE III

Human Cancer Cell Line Studies

In vitro cell binding studies of $^{105}$Rh-BBN-37 with two different human cancer cell lines that express GRP receptors (i.e., the PC-3 and CF-PAC1 cell lines), which are tumor cells derived from patients with prostate CA and pancreatic CA, as shown in FIGS. 17A–B and 18A–B, respectively) were performed. Results of these studies demonstrated consistency with $^{105}$Rh-BBN-37 binding and retention studies using Swiss 3T3 cells. Specifically, the binding affinity of Rh-BBN-37 was high (i.e., IC$_{50}$≅7 nM) with both human cancer cell lines as shown in Table 1. In addition, in all cells, the majority of the $^{105}$Rh-BBN-37 was internalized and perhaps a major unexpected result was that the retention of the $^{105}$Rh-tracer inside of the cells was significantly better than retention in Swiss 3T3 cells as shown in FIGS. 17 and 18. For example, it is particularly remarkable that the percentage of $^{105}$Rh-BBN-37 that remained associated with both the CFPAC-1 and PC-3 cell line was >80% at two hours after removing the extracellular activity by washing with fresh incubation buffer (see FIGS. 17 and 18).

EXAMPLE IV

In Vitro Studies

Biodistribution studies were performed by intravenous (I.V.) injection of either $^{105}$Rh-BBN-22 or $^{105}$Rh-BBN-37 into normal mice. In these studies, unanesthetized CF-1 mice (15–22 g, body wt.) were injected I.V. via the tail vein with between one (1) to five (5) uCi (37–185 KBq) of the $^{105}$Rh-labeled agent. Organs, body fluids and tissues were excised from animals sacrificed at 30, 60 and 120 minutes post-injection (PI). The tissues were weighed, washed in saline (when appropriate) and counted in a NaI well counter. These data were then used to determine the percent injected dose (% ID) in an organ or fluid and the %ID per gram. The whole blood volume of each animal was estimated to be 6.5 percent of the body weight. Results of these studies are summarized in Tables 2 and 3.

Results from these studies showed that both the $^{105}$Rh-BBN-22 and $^{105}$Rh-BBN-37 were cleared from the blood stream, predominantly via the kidney into the urine. Specifically, 68.4±6.6% and 62.3±5.8% of the ID was found in urine at two hours PI of $^{105}$Rh-BBN-22 and $^{105}$Rh-BBN-37, respectively (see Tables 2 and 3). An unexpected finding was that the % ID of $^{105}$Rh that remained deposited in the kidneys of these animals was only 2.4±0.6% ID and 4.6±1.3% ID at two hours PI of $^{105}$Rh-BBN-22 and $^{105}$Rh-BBN-37 (see Tables 2 and 3). This is much less than would be expected from previously reported data where radiometallated peptides and small proteins have exhibited renal retention of the radiometal that is >10% ID and usually much >10% [Duncan et al., 1997]. The reason for reduced renal retention of $^{105}$Rh-BBN analogues is not known, however, this result demonstrates a substantial improvement over existing radiometallated peptides.

Biodistribution studies also demonstrated another important in vivo property of these radiometallated BBN analogues. Both $^{105}$Rh-BBN-22 and $^{105}$Rh-BBN-37 are efficiently cleared from organs and tissues that do not express GRP receptors (or those that do not have their GRP-receptors accessible to circulating blood). The biodistribution studies in mice demonstrated specific uptake of $^{105}$Rh-BBN-22 and $^{105}$Rh-BBN-37 in the pancreas while other non-excretory organs or tissues (i.e., heart, brain, lung, muscle, spleen) exhibited no uptake or retention (Tables 2 and 3). Both $^{105}$Rh-BBN-22 and $^{105}$Rh-BBN-37 were removed from the blood stream by both the liver and kidneys with a large fraction of the $^{105}$Rh removed by these routes being excreted into the intestines and the bladder, respectively. It is important to note that the % ID/gm in the pancreas of $^{105}$Rh-BBN-22 and $^{105}$Rh-BBN-37 was 3.9±1.3% and 9.9±5.4%, respectively at 2 hr, PI. Thus, the ratios of % ID/gm of $^{105}$Rh-BBN-22 in the pancreas relative to muscle and blood were 16.2 and 7.6, respectively. The ratios of % ID/gm of $^{105}$Rh-BBN-37 in the pancreas relative to muscle and blood were 25.4 and 29.1, respectively. These data demonstrated selective in vivo targeting of these radiometallated BBN analogues to cells expressing GRP receptors [Zhu et al., 1991; Qin et al., 1994] and efficient clearance from non-target tissues. If cancer cells that express GRP receptors are present in the body, these results indicate radiometallated BBN analogues will be able to target them with a selectivity similar to the pancreatic cells.

A comparison of the pancreatic uptake and retention of $^{105}$Rh-BBN-22 with $^{105}$Rh-BBN-37 demonstrated that $^{105}$Rh-BBN-37 deposits in the pancreas with a 2-fold better efficiency than $^{105}$Rh-BBN-22 (i.e., 3.6±1.2% ID and 2.3±1.0% ID) for $^{105}$Rh-BBN-37 at one and two hours PI, respectively, vs. 1.2±0.5% ID and 1.0±0.1% ID for $^{105}$Rh-BBN-22 at one and two hours PI). This data is consistent with the >2-fold higher uptake and retention of $^{105}$Rh-BBN-37 found in the in vitro studies shown in FIG. 16.

EXAMPLE V

Figure 19:
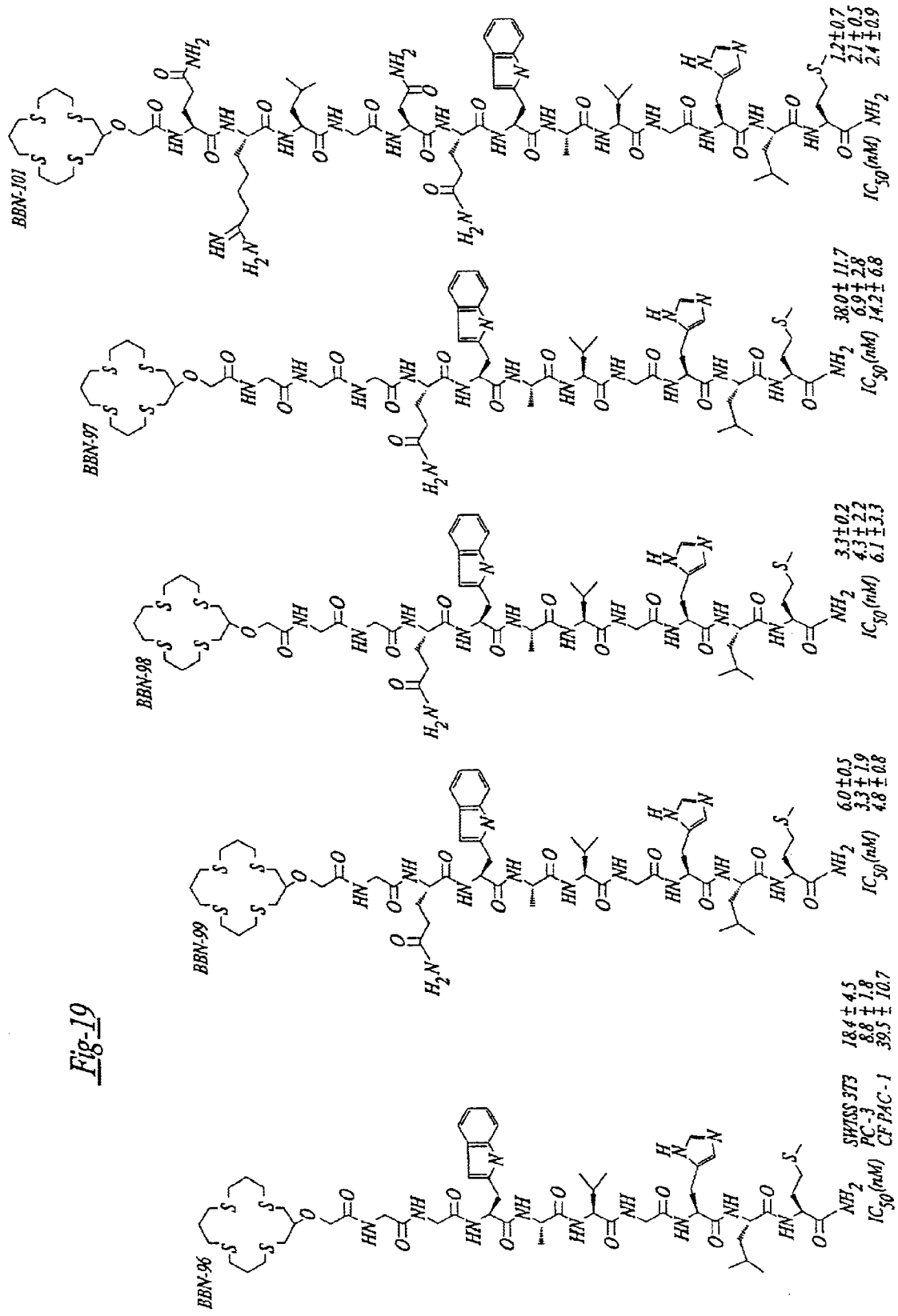
FIG. 19 illustrates 5 [16]aneS$_4$ bombesin analogues.

Synthesis and In Vitro Binding Measurement of Synthetic BBN Conjugate Analogues Employing Amino Acid Chain Spacers A. Synthesis Five BBN analogues were synthesized by SPPS in which between 2 to 6 amino acid spacer groups were inserted to separate a $S_4$-macrocyclic chelator from the N-terminal trp$^8$ on BBN(8–14) (FIG. 19). Each peptide was prepared by SPPS using an Applied Biosystems Model 432A peptide synthesizer. After cleavage of each BBN analogue from the resin using Trifluoracetic acid (TFA), the peptides were purified by $C_{18}$ reversed-phase HPLC using a Vydac HS54 column and $CH_3CN/H_2O$ containing 0.1% TFA as the mobile phase. After collection of the fraction containing the desired BBN peptide, the solvent was evaporated. The identity of each BBN peptide was confirmed by FAB-mass spectrometry (Department of Chemistry—Washington University, St. Louis, Mo.).

Various amino acid sequences (in some cases containing different R group moieties) were conjugated to the N-terminal end of the BBN binding region (i.e., to BBN-8 or Trp$^8$). BBN analogue numbers 96, 97, 98, 99 and 101 were synthesized as examples of N-terminal modified peptides in which the [16]aneS$_4$ macrocycle BFCA was separated from trp$^8$ on BBN(8–14) by various amino acid sequences as shown in FIG. 19.

The [16]aneS$_4$ macrocyclic ligand was conjugated to selected tethered BBN analogues. The —OCH$_2$COOH group on the [16]andS$_4$ macrocycle derivative was activated via HOBt/HBTU so that it efficiently formed an amide bond with the terminal NH2 group on the spacer side arm (following deprotection). The corresponding [16]aneS$_4$ tethered BBN derivatives were produced and examples of 5 of these derivatives (i.e., BBN-96, 97, 98, 99 and 101) are shown in FIG. 19. As previously described, each [16]aneS$_4$ BBN derivative was purified by reversed phase HPLC and characterized by FAB Mass Spectroscopy.

B. In Vitro Binding Affinities

The binding affinities of the synthetic BBN derivatives were assessed for GRP receptors on Swiss 3T3 cells, PC-3 cells and CF PAC-1 cells. The IC$_{50}$'s of each of derivative was determined relative to (i.e., in competition with) $^{125}$I-Tyr$^4$-BBN. The cell binding assay methods used to measure the IC$_{50}$'s is standard and was used by techniques previously reported [Jensen et al., 1993; Cai et al., 1992; Cai et al., 1994]. The methods used for determining IC$_{50}$'s with all BBN analogue binding to GRP repectors present on all three cell lines was similar. The specific method used to measure IC$_{50}$'s on Swiss 3T3 cells is briefly described as follows:

Swiss 3T3 mouse fibroblasts are grown to confluence in 48 well microliter plates. An incubation media was prepared consisting of HEPES (11.916 g/l), NaCl (7.598 g/l), KCl (0.574 g/l), MgCl$_2$(1.106 g/l), EGTA (0.380 g/l), BSA (5.0 g/l), chymostatin (0.002 g/l), soybean trypsin inhibitor (0.200 g/l), and bacitracin (0.050 g/l). The growth media was removed, the cells were washed twice with incubation media, and incubation media was returned to the cells. $^{125}$I-Tyr$^4$-BBN (0.01 µCi) was added to each well in the presence of increasing concentrations of the appropriate competitive peptide. Typical concentrations of displacing peptide ranged from $10^{-12}$ to $10^{-5}$ moles of displacing ligand per well. The cells were incubated at 37° C. for forty minutes in a 95% $O_2$/5% $CO_2$ humidified environment. At forty minutes post initiation of the incubation, the medium was discarded, and the cells were washed twice with cold incubation media. The cells were harvested from the wells following incubation in a trypsin/EDTA solution for five minutes at 37° C. Subsequently, the radioactivity, per well, was determined and the maximum % total uptake of the radiolabeled peptide was determined and normalized to 100%. A similar procedure was used in performing cell binding assays with both the PC-3 and CF$_a$-PAC-1 human cancer cell lines.

C. Results of Binding Affinity Measurements

The IC$_{50}$ values measured for the BBN derivatives synthesized in accordance with this invention showed that appending a chelator via amino acid chain spacer groups via the N-terminal BBN-8 residue (i.e., Trp$^8$) produced a variation of IC$_{50}$ values. For example, see IC$_{50}$ values shown for BBN 96, 97, 98 and 101 in FIG. 19. The observations are consistent with previous reports showing variable IC$_{50}$ values when derivatizing BBH(8–13) with a predominantly short chain of amino acid residues [Hoffken, 1994]. When the amino acid spacer groups used in BBN-98, 99 and 101 were appended between BBN(7–14) and the [16]aneS$_4$ macrocyle, the IC$_{50}$'s were found to be surprisingly constant and in the 1–6 nM range for all three cell lines (i.e., see IC$_{50}$ values shown in FIG. 19). These data suggest that using relatively simple spacer groups composed entirely of selected amino acid sequences to extend ligands some distance from the BBN region [e.g., BBN(8–14) can produce derivatives that maintain binding affinities in the 1–6 nmolar range.

D. Cell Binding Studies with Rh-BBN-Conjugates

Figure 20:
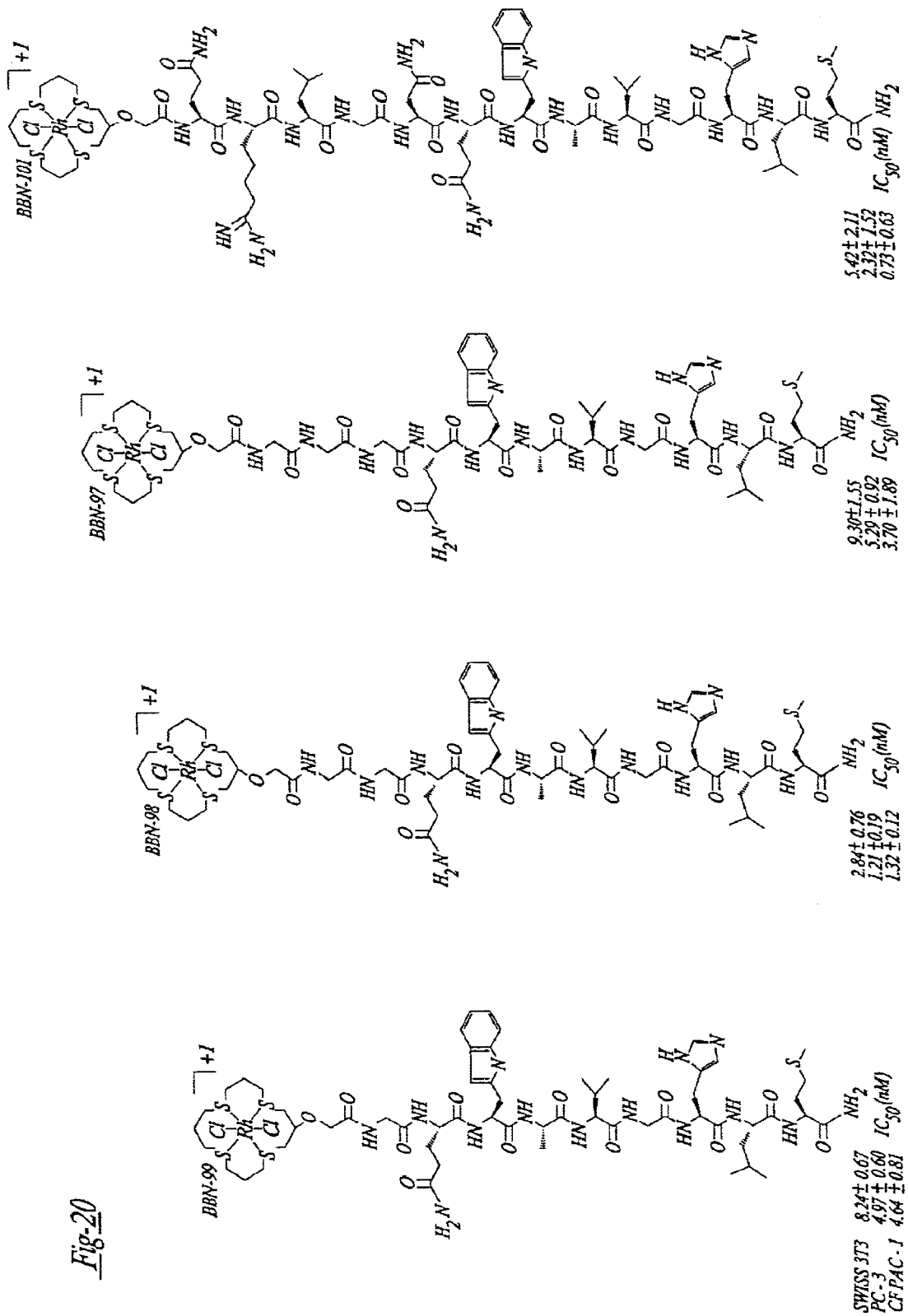
FIG. 20 illustrates 4 Rhodium-[16]aneS$_4$ bombesin analogues.

Results illustrated in FIG. 20 show that when the corresponding RhCl$_2$ [16]aneS$_4$ complex was separated from Trp$^8$ on BBH(8–14) by the four different amino acid spacer groups (see FIG. 20), the IC$_{50}$'s of all four analogues (i.e., BBN-97, -98, -99, -101) were between 0.73 and 5.29 nmolar with GRP receptors on the PC-3 and CF PAC-1 cell lines. The IC$_{50}$'s for these same Rh-BBN conjugates were somewhat higher with the Swiss 3T3 cell line (FIG. 20). These data demonstrate that amino acid chain with spacer groups used to move the +1 charged Rh—S$_4$-chelate away from the BBN binding region will result in a metallated BBN analogue with sufficiently high binding affinities to GRP receptors for in vivo tumor targeting applications.

EXAMPLE VI

Figure 21:
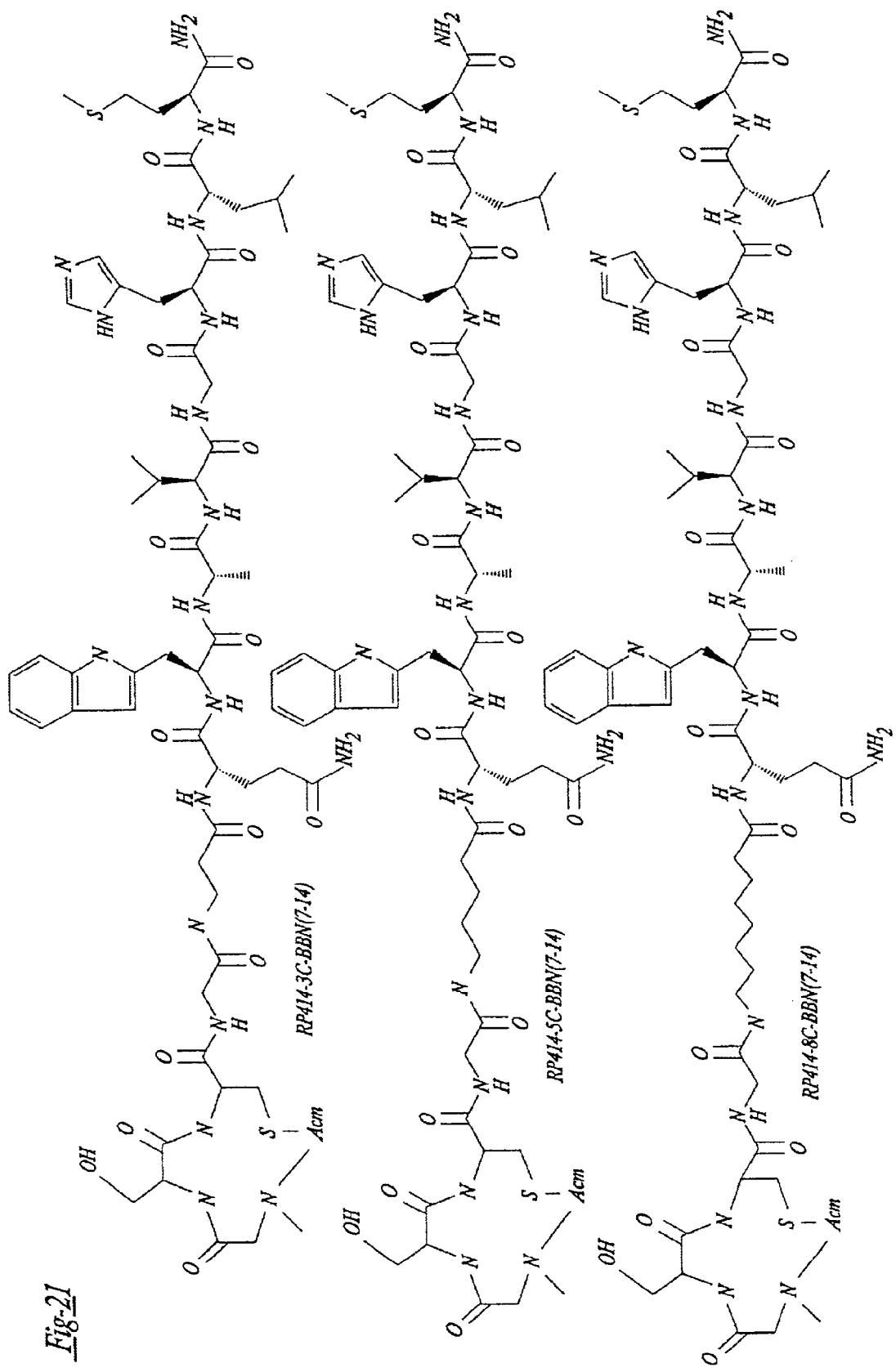
FIG. 21 illustrates 3 different N$_3$S-BFCA conjugates of BBN(7–14).

Synthesis and In Vitro Binding Assessment of a $^{99m}$Tc-Labeled Synthetic BBN Analogue A. Synthesis Several tetradentate chelating frameworks have been used to form stable $^{99m}$Tc or $^{188}$Re labeled peptide and protein conjugates [Eckelman, 1995; Li et al., 1996b; Parker, 1990; Lister-James et al., 1997]. Many of these ligand systems contain at least one thiol (—SH) donor group to maximize rates of formation and stability (both in vitro and in vivo) of the resultant Tc(V) or Re(V) complexes [Parker, 1990; Eckelman, 1995]. Results from a recent report indicates that the bifunctional chelating agent (BFCA) (dimethylglycyl-L-seryl-L-cyteinyl-glycinamide ($N_3$S-BFCA) is capable of forming a well-defined complex with $ReO^{+3}$ and $TcO^{+3}$ [Wong et al., 1997]. Since this ligand framework can be synthesized by SPPS techniques, this $N_3$S-BFCA was selected for use in forming of Tc-99m-BBN-analogue conjugates. Three different $N_3$S-BFCA conjugates of BBN (7–14) were synthesized (BBN-120, -121 and -122) as shown in FIG. 21 by SPPS. BBN-120, BBN-121 and BBN-122 represent a series of analogues where the $N_3$S-BFCA is separated from the BBN(7–14) sequence by a 3, 5 and 8 carbon spacer groups (FIG. 21). Each peptide was synthesized and purified using the SPPS and chromatographic procedures outlined in Example 1. The thiol group on cystein was protected using the ACM group, which is not cleaved during cleavage of these BBN-conjugates from the resin using TFA. The identity of BBN-120, -121 and -122 was confirmed by FAB mass spectrometry. Synthesis and purification of the $N_3$S-BFCA could also be readily accomplished using SPPS methods, followed by HPLC purification (see Example 1). The ACM group was used to protect the thiol group on cysteine during synthesis and cleavage from the resin.

B. In Vitro Binding Affinities

Figure 22:
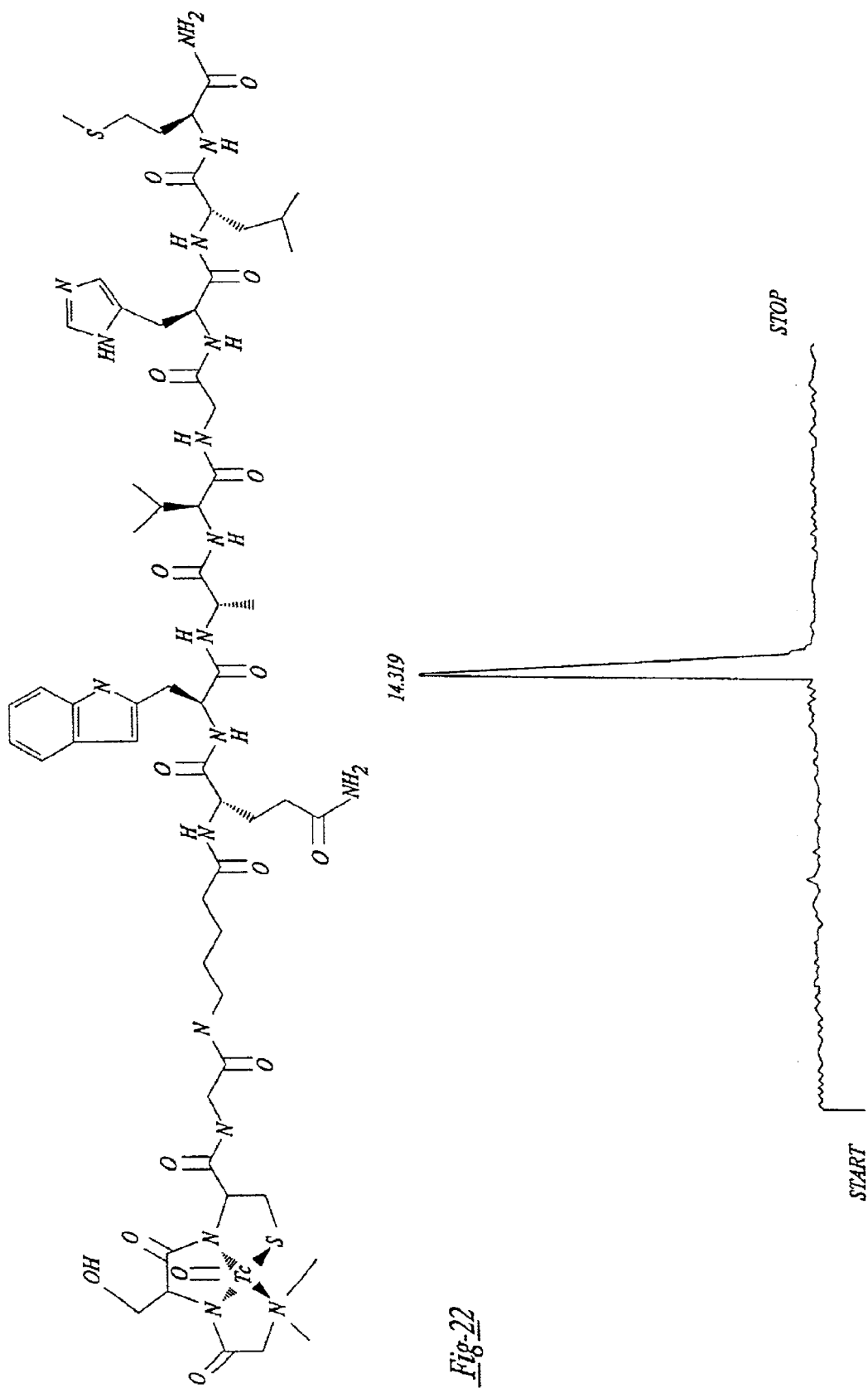
FIG. 22 illustrates on HPLC chromatogram of $^{99m}Tc$-BBN-122.

Synthesis of $^{99m}$Tc-BBN-122 (FIG. 22) was prepared by two methods [i.e., (1) by transchelation of $^{99m}$TcO$^{+3}$ from $^{99m}$Tc-gluconate or (2) by formation of the "preformed" $^{99m}$Tc-BFCA complex followed by —COOH activation with tetrafluorophenyl and subsequent reaction with the $C_5$-carbon spacer group appended to BBN(7–14)]. In both cases, the $^{99m}$Tc-labeled peptide formed is shown in FIG. 22. The structure of this Tc-BBN-122 conjugate was determined by using non-radioactive Re(the chemical congener of Tc). In these studies, the "preformed" $ReO^{+3}$ complex with the $N_3$S-BFCA was prepared by reduction of $ReO_4$; with $SnCl_2$ in the presence of excess $N_3$S-BFCA dissolved in sodium phosphate buffered water at pH 6–6.5 by a method previously published [Wong et al., 1997]. After purification of the ReO—$N_3$S-BFCA complex, the structure of this chelate was shown (by Mass-Spect) to be identical to that previously reported [Wong et al., 1997].

The ReO—$N_3$—S—BFCA complex was converted to the activated trifluorophenyl (TFP) ester by adding 10 mg of the complex to 6 mg (dry) EDC and the 50 μl of TFP. After the solution was vortexed for one minute, $CH_3$CN was added until disappearance of cloudiness. The solution was incubated for one hour at RT and purified by reversed-phase HPLC. To prepare the ReO—$N_3$S-BFCA complex BBN-122 conjugate (FIG. 22), one μl of the HPLC fraction containing the ReO—$N_3$S-BFCA complex was added to a solution containing 1 mg of the $C_8$-tethered BBN(7–14) peptide in 0.2 N NaHCO$_3$ at pH 9.0. After incubation of this solution for one hour at RT, the sample was analyzed and purified by reversed-phase HPLC. The yield of Re-BBN-122 was approximately 30–35%.

The method for preparation of the corresponding $^{99m}$Tc-BBN-122 conjugate, using the "preformed" $^{99m}$TcO—$N_3$S-BFCA complex, was the same as described above with the "preformed" ReO—$N_3$S-BFCA complex. In this case, $^{99m}$TcO$_4$, from a $^{99}$Mo/$^{99m}$Tc generator, was reduced with an aqueous saturated stannous tartrate solution in the presence of excess $N_3$S-BFCA. The yields of the $^{99m}$Tc-BBN-122 product using this "preformed" method were approximately 30–40%. Reversed phase HPLC analysis of the 99mTc-BBN-122, using the same gradient elution program[1] as used for analysis of the Re-BBN-122 conjugate, showed that both the $^{99m}$Tc-BBN-122 and $^{188}$Re-BBN-122 had the same retention time (i.e., 14.2–14.4 min) (See FIG. 22). This provides strong evidence that the structure of both the $^{99m}$Tc-BBN-122 and Re-BBN-122 are identical.

[1] Gradient elution program used in these studies was as follows. Flow 1.5 ml/minute Solvent A=HO with 0.1% TFA Solvent B=CHCN with 0.1% TFA The binding affinities of BBN-122 and Re-BBN-122 were assessed for GRP receptors on Swiss 3T3 cells, PC-3 cells and CFPAC-1 cells that express GRP receptors. The IC$_{50}$'s of each derivative was determined relative to (i.e., in competition with) $^{125}$I-Tyr$^4$-BBN (the K$_d$ for $^{125}$I-Tyr$^4$-BBN for GRP receptors in Swiss 3T3 cells is reported to be 1.6±0.4 nM) [Zhu et al., 1991]. The cell binding assay methods used to measure the IC$_{50}$'s is standard and was used by techniques previously reported [Leban et al., 1994; Cai et al., 1994; Cai et al., 1992]. The methods used for determining IC$_{50}$'s with all GRP receptor binding of GRP receptors on all cell lines was similar and has been described previously for the other BBN-analogues and Rh-BBN analogues described in this document.

C. Results of Binding Affinity Measurements

The IC$_{50}$ values measured for BBN-122 and Re-BBN-122 synthesized in accordance with this invention showed that appending an

| Time (minutes) | % A/% B |
|---|---|
| 0 | 95/5 |
| 25 | 30/70 |
| 35 | 95/5 |

8-carbon hydrocarbon chain spacer linked to the $N_2S_1$-BFCA and the corresponding Re complex (i.e., Trp$^8$) produced BBN conjugates with IC$_{50}$ values in a 1–5 nmolar range (See Table A). When $^{99m}$Tc-BBN-122 was incubated with these same cells, it was shown that ≧nmolar concentrations of BBN displaced this $^{99m}$Tc conjugate by >90%. This result demonstrates that $^{99m}$Tc-BBN-122 has high and specific binding affinity for GRP receptors. These data suggest that using relatively simple spacer groups to extend the $N_3$S ligand framework and the corresponding Tc— or Re—$N_3S_1$, complexes some distance from the BBN binding region can produce derivatives that maintain binding affinities in the 1–5 nmolar range.

TABLE A.

Summary of IC$_{50}$ values for GRP receptor binding for the non-metallated BBN-122 conjugate or the Re-BBN-122 conjugate in two cell lines (PC-3 and CF-PAC-1 cell lines that express GRP receptors). The IC$_{50}$ values were measured using cell binding assays relative to $^{125}$I-Tyr$^4$-BBN.

| | IC$_{50}$ (nmolar) | |
|---|---|---|
| Conjugate | PC-3 | CF-PAC1 |
| BBN-122 | 3.59 ± 0.75 (n = 6) | 5.58 ± 1.92 (n = 14) |
| Re-BBN-122 | 1.23 ± 0.56 (n = 12) | 1.47 ± 0.11 (n = 6) |

EXAMPLE VII

Retention of 99m Tc-BBN-122 in Human Cancer Cells PC-3 and CF-PAC-1 Cells

Once the radiometal has been specifically "delivered" to cancer cells (e.g., employing the BBN binding moiety that specifically targets GRP receptors on the cell surface), it is necessary that a large percentage of the "delivered" radioactive atoms remain associated with the cells for a period time of hours or longer to make an effective radiopharmaceutical for effectively treating cancer. One way to achieve this association is to internalize the radiolabeled BBN conjugates within the cancer cell after binding to cell surface GRP receptors.

Experiments designed to determine the fraction $^{99m}$Tc-BBN-122 internalized within cells were performed by the same method previously described for $^{105}$Rh-BBN-37. Briefly, excess $^{99m}$Tc-BBN-122 was added to PC-3 or CFPAC-1 cell incubation media and allowed to establish equilibrium after a forty minute incubation. The media surrounding the cells was removed and the cells were washed with fresh media containing no radioactivity. After washing, the quantity of radioactivity associated with the cells was determined (i.e., total counts per min $^{99m}$Tc associated with cells). The PC-3 and CFPAC-1 cells were then incubated in a 0.2M acetic acid solution (pH 2.5) which caused the surface proteins (including GRP receptors) to denature and release all surface bound radioactive materials. After removing this buffer and washing, the cells were counted again. The counts per minute (c.p.m.) associated with the cells at that point were only related to the $^{99m}$Tc that remained trapped inside of the PC-3 or CFPAC-1 cells.

To determine intracellular retention of $^{99m}$Tc activity, a similar method was employed. However, after washing the cells with fresh (non-radioactive) incubation media, the cells were incubated in the fresh media at different time period after washing away all extracellular $^{99m}$Tc-BBN-122. After each time interval, the methods used to determine total c.p.m. and intracellular c.p.m. by washing with a 0.2M acetic acid solution at pH 2.5.

Figure 23:
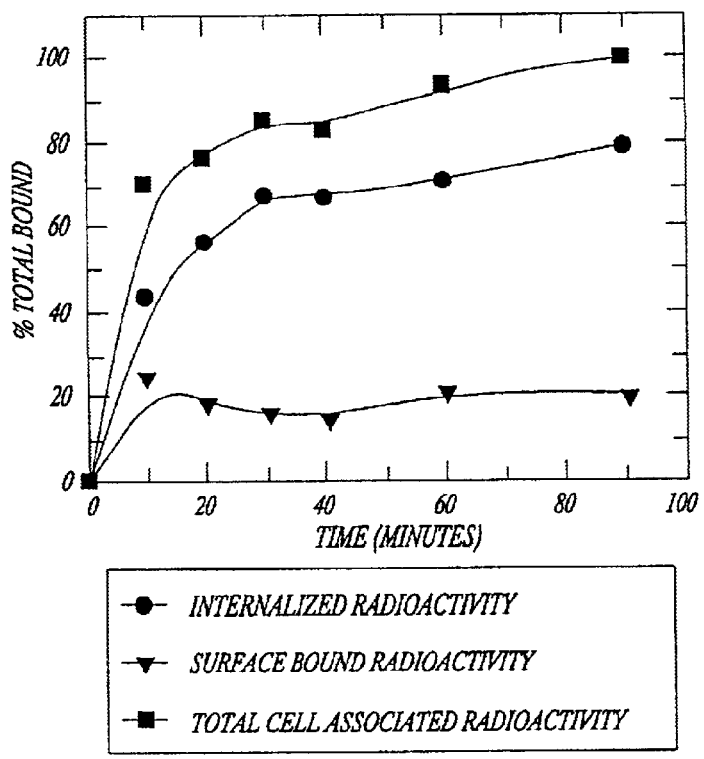
FIG. 23 is a graph illustrating $^{99m}TC$-BBN-122 internalization efflux from human prostate cancer cells (PC-3 cells).
Figure 24:
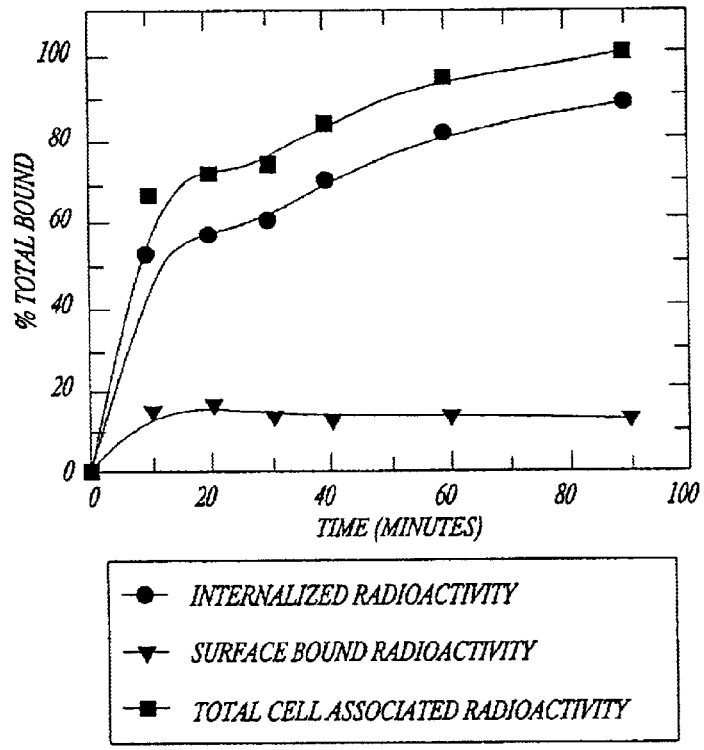
FIG. 24 is a graph illustrating $^{99m}Tc$-BBN-122 internalization efflux from human pancreatic tumor cells (CFPAC-1 cells).
Figure 25:
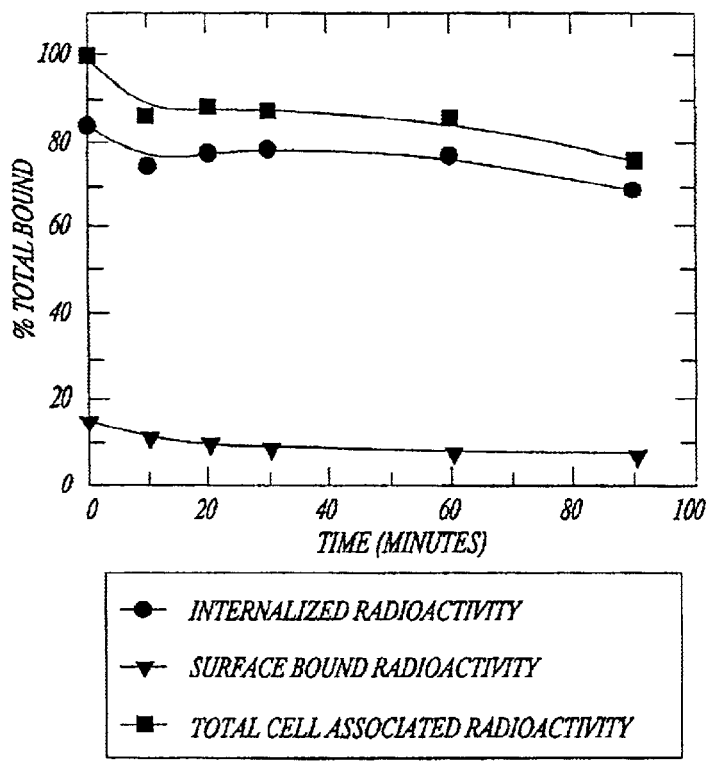
FIG. 25 is a graph illustrating $^{99m}Tc$-RP-414-BBN-42 retention in PC-3 prostate cancer cells.
Figure 26:
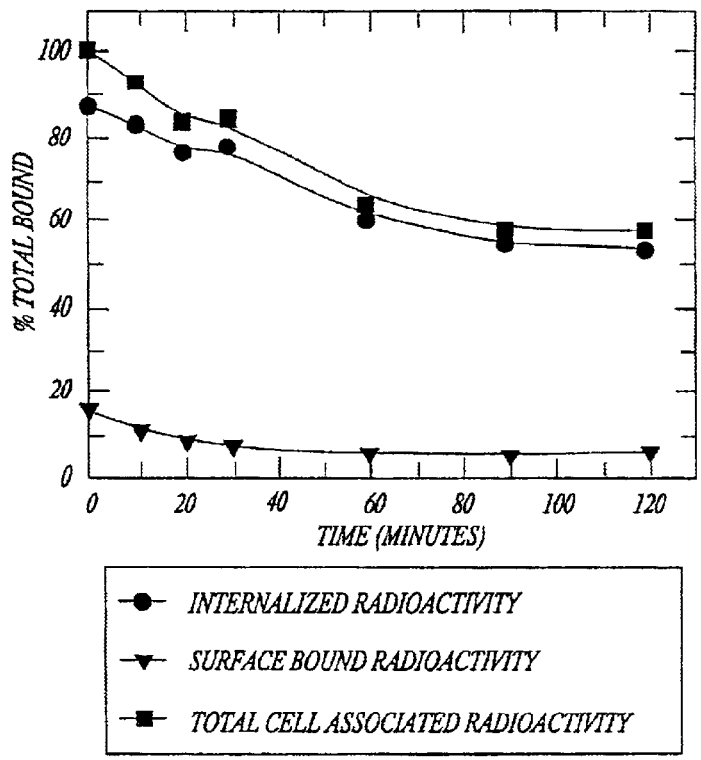
FIG. 26 is a graph illustrating 99mTc-42 retention in CFPAC-1 pancreatic cancer cells.

Studies with the 99mTc-BBN-122 agonist show that it is internalized inside of the PC-3 and CFPAC-1 cells (FIGS. 23–26) and that substantial intracellular retention of $^{99m}$Tc by the GRP receptor expressing cells occurs. For example, results of studies using $^{99m}$Tc-BBN-122 in conjunction with PC-3 cells showed a high rate of internalization (FIG. 23) and that approximately 75% of the $^{99m}$Tc activity remains associated with the cells at ninety minutes post-washing (FIG. 25). Almost all of this $^{99m}$Tc cell-associated activity is inside of the PC-3 cells. Similar results were also found with the CFPAC 1 cells where there is also a high rate of $^{99m}$Tc-BBN-122 internalization (FIG. 24) and relatively slow efflux of $^{99m}$Tc from the cells (i.e., 50–60% retention at 120 min post-washing (FIG. 26).

The $^{99m}$Tc-BBN-122 peptide conjugate shown in FIG. 22 has an amidated methionine at position BBN-14 and is expected to be an agonists [Jensen et al., 1993]. Therefore, it would be predicted to rapidly internalize after binding to GRP receptors on the cell surface [Bjisterbosch et al., 1995; Smythe et al., 1991], which is confirmed by applicants' data in FIG. 23–26.

EXAMPLE VIII

In Vivo Studies

Biodistribution studies were performed by intravenous (I.V.) injection of $^{99m}$Tc-BBN-122 into normal mice. In these studies, unanesthetized CF-1 mice (15–22 g, body wt.) were injected I.V. via the tail vein with between one (1) to five (5) μCi (37–185 KBq) of $^{99m}$Tc-BBN-122. Organs, body fluids and tissues were excised from animals sacrificed at 0.5, 1, 4 and 24 hours post-injection (PI). The tissues were weighed, washed in saline (when appropriate) and counted in a NaI well counter. These data were then used to determine the percent injected dose (% ID) in an organ or fluid and the % ID) per gram. The whole blood volume of each animal was estimated to be 6.5 percent of the body weight. Results of these studies are summarized in Tables B and C.

Results from these studies showed that 99mTc-BBN-122 is cleared from the blood stream predominantly via the hepatobiliary pathway shaving about 35% of the $^{99m}$Tc-activity cleared via the kidney into the urine. Specifically, 33.79±1.76% of the ID was found in urine at one hour PI (Table B). The retention of $^{99m}$Tc activity in the kidneys and liver is very low (Table B). This is much less than would be expected from previously reported data where radiometallated peptides and small proteins have exhibited renal retention of the radiometal that is >10% ID and usually much >10% [Duncan et al., 1997]. The reason for reduced renal retention of $^{99m}$Tc-BBN-122 is not known, however, this result demonstrates a substantial improvement over existing radiometallated peptides.

Biodistribution studies also demonstrated another important in vivo property of $^{99m}$Tc-BBN-122 in that it is efficiently cleared from organs and tissues that do not express GRP receptors (or those that do not have their GRP-receptors accessible to circulating blood). The biodistribution studies in mice demonstrated specific uptake of $^{99m}$Tc-BBN-122 in the pancreas while other non-excretory organs or tissues (i.e., heart, brain, lung, muscle, spleen) exhibited no uptake or retention. $^{99m}$Tc-BBN-122 is removed from the blood stream by both the liver and kidneys with a large fraction of the 99mTc removed by these routes being excreted into the intestines and the bladder, respectively. It is important to note that the % ID/gm in the pancreas of $^{99m}$Tc-BBN-122 is 12.63%/gm at 1 hour and drops to only 5.05% at the 4 hour PI (Table C). Thus, the ratios of % ID/gm of $^{99m}$Tc-BBN-122 in the pancreas relative to muscle and blood were 92.2 and 14.78 at 4 hour PI, respectively. These data demonstrated selective in vivo targeting of this $^{99m}$Tc-labeled BBN analogue to cells expressing GRP receptors [Zhu et al., 1991; Qin et al., 1994] and efficient clearance from non-target tissues. If cancer cells that express GRP receptors are present in the body, these results indicate 99mTc-BBN analogues will be able to target them with a selectivity similar to the pancreatic cells.

TABLE B

Biodistribution of $^{99m}$Tc-BBN-122 in normal CF-1 mice at 0.5, 1, 4 and 24 hr post-IV injection. Results expressed as % ID/organ

| | % Injected Dose/Organ[a] | | | |
|---|---|---|---|---|
| Organ[c] | 30 min | 1 hr | 4 hr | 24 hr |
| Blood[d] | 3.52 ± 2.16 | 1.08 ± 0.34 | 0.59 ± 0.24 | 0.12 ± 0.01 |
| Liver | 4.53 ± 0.93 | 4.77 ± 1.40 | 1.49 ± 0.32 | 0.32 ± 0.06 |
| Stomach | 2.31 ± 0.45 | 1.61 ± 0.81 | 1.75 ± 0.20 | 0.30 ± 0.06 |
| Lg. Intestine[b] | 2.84 ± 0.32 | 24.17 ± 7.91 | 23.85 ± 7.02 | 0.61 ± 0.14 |
| Sm. Intestine[b] | 43.87 ± 1.51 | 23.91 ± 9.08 | 5.87 ± 7.09 | 0.42 ± 0.06 |
| Kidneys[b] | 1.49 ± 0.19 | 1.15 ± 0.10 | 0.55 ± 0.06 | 0.20 ± 0.01 |
| Urine[b] | 26.78 ± 1.05 | 33.79 ± 1.76 | ~35 | ~35 |
| Muscle | 0.02 ± 0.01 | 0.01 ± 0.00 | 0.01 ± 0.01 | 0.01 ± 0.01 |
| Pancreas | 5.30 ± 0.63 | 3.20 ± 0.83 | 1.21 ± 0.13 | 0.42 ± 0.17 |

[a]Each value in the table represents the mean and SD from 5 animals in each group.
[b]At 4 and 24 hr, feces containing $^{99m}$Tc had been excreted from each animal and the % ID in the urine was estimated to be approximately 60% of the ID.
[c]All other organs excised (incl. brain, heart, lung and spleen) showed <0.10% at t ≧ 1 hr.
[d]% ID in the blood estimated assuming the whole blood volume is 6:5% of the body weight.

TABLE C

Biodistribution of $^{99m}$Tc-BBN-122 in normal CF-1 mice at 0.5, 1, 4 and 24 hr post I.V. injection. Results expressed as % ID/gm.

| Organ | % Injected Dose/gm[a] | | | |
|---|---|---|---|---|
| | 30 min | 1 hr | 4 hr | 24 hr |
| Blood[b] | 2.00 ± 1.28 | 0.63 ± 0.19 | 0.34 ± 0.11 | 0.08 ± 0.00 |
| Liver | 2.70 ± 0.41 | 3.14 ± 0.81 | 0.96 ± 0.20 | 0.22 ± 0.05 |
| Kidneys | 3.99 ± 0.76 | 3.10 ± 0.31 | 1.58 ± 0.15 | 0.64 ± 0.08 |
| Muscle | 0.23 ± 0.08 | 0.13 ± 0.02 | 0.05 ± 0.01 | 0.01 ± 0.01 |
| Pancreas | 16.89 ± 0.95 | 12.63 ± 1.87 | 5.05 ± 0.42 | 1.79 ± 0.71 |
| P/Bl and P/M Uptake Ratios | | | | |
| Pancreas/Blood | 8.42 | 19.76 | 14.78 | 20.99 |
| Pancreas/Muscle | 73.16 | 93.42 | 92.25 | 142.76 |

[a]Each value in the table represents the mean and SD from 5 animals in each group.
[b]% ID in the blood estimated assuming the whole blood volume is 6:5% of the body weight.

TABLE D

Biodistribution of $^{99m}$Tc-BBN-122 in PC-3 tumor bearing SCID mice at 1, 4 and 24 hr post-I.V. injection. Results expressed as % ID/organ.

| Tumor Line: PC-3 | % ID per Organ[a] | | |
|---|---|---|---|
| Organ[c] | 1 hr | 4 hr | 24 hr |
| Blood[b] | 1.16 ± 0.27 | 0.47 ± 0.06 | 0.26 ± 0.05 |
| Liver | 1.74 ± 0.64 | 0.72 ± 0.10 | 0.29 ± 0.05 |
| Stomach | 0.43 ± 0.18 | 0.29 ± 0.22 | 0.08 ± 0.02 |
| Lg. Intestine | 9.18 ± 19.42 | 42.55 ± 8.74 | 0.64 ± 0.17 |
| Sm. Intestine | 46.55 ± 16.16 | 2.13 ± 0.76 | 0.31 ± 0.04 |
| Kidneys | 1.16 ± 0.20 | 0.60 ± 0.06 | 0.16 ± 0.01 |
| Urine[d] | 32.05 ± 12.78 | ~35 | ~35 |
| Muscle | 0.01 ± 0.00 | 0.00 ± 0.00 | 0.00 ± 0.00 |
| Pancreas | 1.69 ± 0.61 | 1.05 ± 0.13 | 0.34 ± 0.08 |
| Tumor | 1.00 ± 0.78 | 0.49 ± 0.08 | 0.49 ± 0.25 |

[a]Each value in the table represents the mean and SD from 5 animals in each group.
[b]At 4 and 24 hr, feces containing $^{99m}$Tc had been excreted from each animal and the % ID in the urine was estimated to be approximately 60% of the ID.
[c]All other organs excised (incl. brain, heart, lung and spleen) showed <0.10% at t ≥ 1 hr.
[d]% ID in the blood estimated assuming the whole blood volume is 6:5% of the body weight.

TABLE E

Biodistribution of $^{99m}$Tc-BBN-122 in PC-3 tumor bearing SCID mice at 1, 4 and 24 hr post-I.V. injection. Results expressed as % ID/Gm.

| Tumor Line: PC-3 | % ID per gm[a] | | |
|---|---|---|---|
| Organ | 1 hr | 4 hr | 24 hr |
| Blood[b] | 0.97 ± 0.26 | 0.31 ± 0.03 | 0.18 ± 0.04 |
| Liver | 2.07 ± 0.88 | 0.64 ± 0.05 | 0.26 ± 0.04 |
| Kidneys | 4.80 ± 1.33 | 2.23 ± 0.35 | 0.60 ± 0.04 |
| Muscle | 0.18 ± 0.12 | 0.06 ± 0.03 | 0.05 ± 0.04 |
| Pancreas | 10.34 ± 3.38 | 5.08 ± 1.12 | 1.47 ± 0.23 |
| Tumor | 2.07 ± 0.50 | 1.75 ± 0.61 | 1.28 ± 0.22 |
| T/Bl, T/M, P/Bl and P/M Uptake Ratios | | | |
| Tumor/Blood | 2.13 | 5.52 | 6.79 |
| Tumor/Muscle | 11.44 | 25.38 | 21.62 |
| Pancreas/Blood | 10.64 | 15.96 | 7.81 |

TABLE E-continued

Biodistribution of $^{99m}$Tc-BBN-122 in PC-3 tumor bearing SCID mice at 1, 4 and 24 hr post-I.V. injection. Results expressed as % ID/Gm.

| Tumor Line: PC-3 | % ID per gm[a] | | |
|---|---|---|---|
| Organ | 1 hr | 4 hr | 24 hr |
| Pancreas/Muscle | 57.14 | 73.40 | 24.87 |

[a]Each value in the table represents the mean and SD from 5 animals in each group.
[b]% ID in the blood estimated assuming the whole blood volume is 6:5% of the body weight.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

Throughout this application, various publications are referenced by citation and number. Full citations for the publication are listed below. The disclosure of these publications in their entireties are hereby incorporated by reference into this application in order to more fully describe the state of the art to which this invention pertains.

REFERENCES CITED

Albert et al., (1991) Labeled Polypeptide Derivatives, Int'l Patent No. WO91/01144.
Bjisterbosch, M. K., et al., (1995) Quarterly J. Nucl. Med. 39:4–19.
Bushbaum, (1995) Pharmacokinetics of Antibodies and Their Radiolabels. In: Cancer Therapy with Radiolabeled Antibodies, (ed) D. M. Goldenberg, CRC Press, Boca Raton, Chaper 10, 115–140 Fla.
Cai et al., (1994) Proc. Natl. Acad. Sci., 91:12664.
Cai et al., (1992) Peptides, 13:267.
Coy et al., (1988) J. Biolog. Chem., 263(11), 5066.
Davis et al. (1992) Peptides, 13:401.
de Jong et al., (1997) Eur. J. Nucl. Med., 24:368.
Duncan et al., (1997) Cancer Res. 57:659.
Eckelman (1995) Eur. J. Nucl. Med., 22:249.
Eckelman et al., (1993) The design of site-directed radiopharmaceuticals for use in drug discovery. In: Nuclear Imaging in Drug Discovery. Development and Approval (eds) H. D. Burns et al., Birkhauser Publ. Inc., Boxton, Mass.
Fischman et al., (1993) J. Nucl. Med., 33:2253.
Frizberg et al. (1995) Radiolabeling of antibodies for targeted diagnostics. In: Targeted Delivery of Imaging Agents (ed) V. P. Torchilin, CRC Press, Boca Raton, Fla., pp. 84–101.
Fritzberg et al., (1992) J. Nucl. Med., 33:394.
Hermanson (1996) In: Bioconjugate Techniques, Academic Press, pp. 3–136.
Hoffken, (ed) (1994) Peptides in Oncology II, Springer-Verlag, Berlin-Heidelberg.
Hoffman, et al., (1997) Quarterly J. Nucl. Med. 41(2) Supp. #1, 5.
Jensen et al., (1993) Rec. Result. Cancer Res., 129:87.
Krenning et al., (1994) Semin. Oncology 5–14.

Leban et al. (1994) *J. Med. Chem.*, 37:439.
Li et al., (1996a) *J. Nucl. Med.*, 37:61P.
Li et al., (1996b) *Radiochim Acta*, 75:83.
Lister-James et al. (1997) *Quart. J. Nucl. Med.*, 41:111.
Lowbertz et al., (1994) *Semin. Oncol.*, 1–5.
Mattes, (1995) Pharmacokinetics of antibodies and their radiolabels. In: *Cancer Therapy with Radiolabeled Antibodies* (ed) D. M. Goldenberg, CRC Press, Boca Raton, Fla.
Moody et al., (1996) *Peptides*, 17(8), 1337.
Moody et al., (1995) *Life Sciences*, 56(7), 521.
Parker (1990) *Chem. Soc. Rev.*, 19:271.
Pollak et al., (1996) *Peptide Derived Radionuclide Chealtors*, Int'l Patent No. WO96/03427.
Qin et al., (1994) *J. Canc. Res. Clin. Oncol.*, 120:519.
Qin, Y. et al., (1994) *Cancer Research* 54: 1035–1041.
Reile, H. et al., (1994) *Prostate* 25: 29–38.
Schubiger et al., (1996) *Bioconj. Chem.*
Seifert et al. (1998) *Appl. Radiat. Isot.*, 49:5.
Smith et al., (1997) *Nucl. Med. Biol.*, 24:685.
Smythe, E. et al., (1991) *Eur. J. Biochem.* 202: 689–699.
Trounter (1987) *Nucl. Med. Biol.*, 14:171.
Vallabhajosula et al., (1996) *J. Nucl. Med.*, 37:1016.
Wilbur (1992) *Bioconj. Chem.*, 3:433.
Wong, E. et al., (1997) *Inorg. Chem.* 36: 5799–5808.
Zhu, W-Y. et al., (1991) *Am. J. Physiol.* 261: G57–64.

TABLE 1

Binding Affinity of Rh-BBN-37 for GRP Receptors Expressed on Neoplasms

| Type of Cancer | Cell Line | IC$_{50}$ (Mean Value) |
|---|---|---|
| Pancreatic CA | CF PAC1 | $3.2 \times 10^{-9}$ |
| Prostate CA | PC-3 | $7.0 \times 10^{-9}$ |

TABLE 2

| | (% Dose) | | |
|---|---|---|---|
| Complex Organ (% Dose) | $^{105}$Rh-Peptide22 30 min n-9 | $^{105}$Rh-Peptide22 1 hr n-9 | $^{105}$Rh-Peptide22 2 hr n-9 |
| Brain | 0.08 ± 0.02 | 0.04 ± 0.01 | 0.06 ± 0.09 |
| Blood | 4.48 ± 1.24 | 1.86 ± 0.38 | 0.99 ± 0.24 |
| Heart | 0.13 ± 0.03 | 0.08 ± 0.03 | 0.04 ± 0.04 |
| Lung | 0.25 ± 0.08 | 0.20 ± 0.09 | 0.15 ± 0.09 |
| Liver | 7.97 ± 2.85 | 8.51 ± 2.33 | 8.57 ± 2.04 |
| Spleen | 0.07 ± 0.03 | 0.09 ± 0.08 | 0.05 ± 0.01 |
| Stomach | 1.11 ± 0.76 | 0.59 ± 0.21 | 0.30 ± 0.16 |
| Large Intestine | 0.73 ± 0.16 | 3.21 ± 3.38 | 8.91 ± 3.79 |
| Small Intestine | 6.29 ± 1.87 | 6.98 ± 1.87 | 3.48 ± 1.78 |
| Kidneys | 4.25 ± 1.33 | 3.25 ± 0.60 | 2.44 ± 0.64 |
| Bladder | 44.66 ± 7.29 | 62.88 ± 3.84 | 68.41 ± 6.63 |
| Muscle | 0.06 ± 0.03 | 0.03 ± 0.03 | 0.01 ± 0.01 |
| Pancreas | 0.95 ± 0.46 | 1.15 ± 0.49 | 1.01 ± 0.14 |
| Carcass | 32.90 ± 6.61 | 12.62 ± 4.77 | 6.37 ± 1.17 |

TABLE 2-continued

| | (% Dose/Gm) | | |
|---|---|---|---|
| Complex Organ (% D/GM) | $^{105}$Rh-Peptide22 30 min n-9 | $^{105}$Rh-Peptide22 1 hr n-9 | $^{105}$Rh-Peptide22 2 hr n-9 |
| Brain | 0.21 ± 0.07 | 0.14 ± 0.08 | 0.16 ± 0.28 |
| Blood | 2.22 ± 0.40 | 1.02 ± 0.22 | 0.51 ± 0.11 |
| Heart | 0.92 ± 0.25 | 0.64 ± 0.20 | 0.38 ± 0.33 |
| Lung | 1.44 ± 0.33 | 1.24 ± 0.54 | 0.92 ± 0.69 |
| Liver | 4.33 ± 1.52 | 5.18 ± 1.52 | 5.17 ± 1.12 |
| Spleen | 0.86 ± 0.38 | 1.10 ± 0.65 | 0.84 ± 0.53 |
| Stomach | 2.46 ± 1.65 | 1.53 ± 0.74 | 0.71 ± 0.33 |
| Large Intestine | 0.78 ± 0.19 | 4.42 ± 4.62 | 10.10 ± 4.58 |
| Small Intestine | 4.73 ± 1.47 | 5.84 ± 1.81 | 2.86 ± 1.47 |
| Kidneys | 7.57 ± 1.49 | 6.70 ± 0.75 | 4.60 ± 0.83 |
| Muscle | 0.53 ± 0.32 | 0.61 ± 0.97 | 0.24 ± 0.24 |
| Pancreas | 3.12 ± 0.99 | 4.31 ± 1.98 | 3.88 ± 1.25 |

TABLE 3

| | (% Dose) | | |
|---|---|---|---|
| Complex Organ (% Dose) | $^{105}$Rh-Pept37 30 min n-5 | $^{105}$Rh-Pept37 1 hr n-9 | $^{105}$Rh-Pept37 2 hr n-7 |
| Brain | 0.03 ± 0.01 | 0.07 ± 0.11 | 0.03 ± 0.03 |
| Blood | 3.09 ± 0.54 | 1.46 ± 0.62 | 0.66 ± 0.26 |
| Heart | 0.12 ± 0.03 | 0.05 ± 0.03 | 0.04 ± 0.02 |
| Lung | 0.26 ± 0.09 | 0.12 ± 0.07 | 0.08 ± 0.11 |
| Liver | 13.04 ± 1.93 | 13.00 ± 3.59 | 10.12 ± 1.86 |
| Spleen | 0.21 ± 0.13 | 0.16 ± 0.08 | 0.10 ± 0.04 |
| Stomach | 0.80 ± 0.34 | 0.65 ± 0.52 | 0.83 ± 0.96 |
| Large Intestine | 2.05 ± 0.69 | 2.96 ± 1.67 | 8.07 ± 2.25 |
| Small Intestine | 8.44 ± 1.89 | 11.38 ± 3.02 | 5.04 ± 2.27 |
| Kidneys | 7.82 ± 2.52 | 6.04 ± 1.68 | 4.57 ± 1.29 |
| Bladder | 39.65 ± 7.21 | 51.82 ± 7.53 | 62.32 ± 5.78 |
| Muscle | 0.06 ± 0.03 | 0.02 ± 0.01 | 0.02 ± 0.02 |
| Pancreas | 2.73 ± 1.14 | 3.63 ± 1.22 | 2.25 ± 1.02 |
| Carcasss | 24.35 ± 7.69 | 9.81 ± 2.91 | 6.37 ± 1.73 |

| | (% Dose/Gm) | | |
|---|---|---|---|
| Complex Organ (% D/GM) | $^{105}$Rh-Pept37 30 min n-5 | $^{105}$Rh-Pept37 1 hr n-9 | $^{105}$Rh-Pept37 2 hr n-7 |
| Brain | 0.10 ± 0.05 | 0.26 ± 0.41 | 0.10 ± 0.09 |

TABLE 3-continued

| | | | |
|---|---|---|---|
| Blood | 1.60 ± 0.30 | 0.72 ± 0.31 | 0.34 ± 0.15 |
| Heart | 0.92 ± 0.26 | 0.38 ± 0.21 | 0.28 ± 0.17 |
| Lung | 1.52 ± 0.48 | 0.76 ± 0.47 | 0.46 ± 0.50 |
| Liver | 7.31 ± 1.15 | 7.65 ± 1.29 | 6.30 ± 1.73 |
| Spleen | 2.18 ± 1.17 | 1.59 ± 0.71 | 1.05 ± 0.44 |
| Stomach | 1.53 ± 0.67 | 1.63 ± 1.17 | 2.18 ± 2.35 |
| Large Intestine | 2.46 ± 0.70 | 3.80 ± 2.42 | 11.84 ± 4.39 |
| Small Intestine | 5.69 ± 1.26 | 7.85 ± 1.87 | 3.81 ± 2.01 |
| Kidneys | 14.28 ± 2.84 | 11.21 ± 3.68 | 8.39 ± 2.36 |
| Muscle | 0.73 ± 0.39 | 0.20 ± 0.14 | 0.39 ± 0.38 |
| Pancreas | 14.02 ± 3.23 | 15.54 ± 6.21 | 9.91 ± 5.35 |

What is claimed is:

1. A compound comprising a metal complexed with a chelating group attached to a gastrin releasing peptide (GRP) receptor agonist, said gastrin releasing peptide receptor agonist including a bombesin agonist-binding moiety.

2. A compound as set forth in claim 1, wherein said chelating group is attached to said bombesin agonist binding moiety by a spacer group.

3. A compound as set forth in claim 2 having a structure of the formula:

X—Y—B

Wherein X is said metal complexed with a chelating group; Y is said spacer group or covalent bond; and B is a bombesin agonist binding moiety.

4. A compound as set forth in claim 3, wherein Y is a $C_1$–$C_{10}$ hydrocarbon chain.

5. A compound as set forth in claim 4, wherein Y is a $C_3$–$C_9$ hydrocarbon chain.

6. A compound as set forth in claim 3, wherein Y comprises at least one amino acid residue.

7. A compound as set forth in claim 6, wherein Y comprises a L-Gln residue at the BBN-7 position.

8. A compound as set forth in claim 2, wherein said chelating group is attached to said bombesin agonist binding moiety at the N-terminal end of a peptide bombesin binding moiety.

9. A compound as set forth in claim 8, wherein said chelating group is attached to said peptide bombesin agonist binding moiety at amino acid residue 8 ($trp^8$) of said bombesin agonist binding moiety.

10. A compound as set forth in claim 8, wherein said spacer is attached to said bombesin agonist binding moiety at the N-terminal end of said bombesin agonist binding moiety.

11. A compound as set forth in claim 10, wherein said spacer is attached to said bombesin agonist binding moiety at amino acid residue 8 ($D^{31}$ or $L^{31}$ $trp^8$) of said bombesin agonist binding moiety.

12. A compound as set forth in claim 1, wherein said metal is a diagnostically or therapeutically useful metal.

13. A compound as set forth in claim 12, wherein said transition metal is a metallic radioisotope selected from the group consisting of γ and β emitting isotopes.

14. A compound as set forth in claim 13, wherein said metallic radioisotope is a radionuclide selected from the group consisting of $^{186}$Re, $^{188}$Re, $^{99mm}$Tc, $^{105}$Rh, $^{199}$Au, $^{153}$Sm, $^{166}$Ho and $^{90}$Y.

15. The compound as set forth in claim 13, wherein said metallic isotope comprises oxides and nitrides thereof.

16. A compound as set forth in claim 1 wherein said chelating agent comprises a multidentate chelating structure capable of forming a highly stable complex with metals via coordinating atoms.

17. A compound as set forth in claim 16, wherein said chelating structure is selected from the group consisting of coordinating atoms S, N, O, or P.

18. A compound as set forth in claim 16, wherein said chelating structure is a macrocyclic compound comprising coordinating atoms.

19. A compound as set forth in claim 16, wherein said chelating structure is a $S_4$ chelator.

20. A compound as set forth in claim 16, wherein said compound is a $N_4$ chelator.

21. A compound as set forth in claim 16, wherein said compound is a $N_2S_2$ chelator.

22. A compound as set forth in claim 16, wherein said compound is a $NS_3$ chelator.

23. A compound as set forth in claim 16, wherein said compound is a $N_3S$ chelator.

24. A compound as set forth in claim 1, wherein said compound has a binding affinity for the gastrin releasing peptide receptor that is approximately equal to or greater than that of native bombesin.

25. A method of forming a therapeutic or diagnostic compound comprising the step of reacting a metal complexed with a chelating group with a gastrin releasing peptide receptor agonist, the gastrin releasing peptide receptor agonist including a bombesiri agonist-binding moiety.

26. A method of forming a therapeutic or diagnostic compound comprising the step of reacting a metal with a chelating group already covalently attached to a gastrin releasing peptide receptor agonist, the gastrin releasing peptide receptor agonist including a bombesin agonist-binding moiety.

27. A method as set forth in claim 25, wherein the compound nas a binding affinity for the gastrin releasing peptide receptor that is approximately equal to or greater than that of native bombesin.

28. A method of formulation a pharmaceutical using a kit type method wherein the metal is added to a sealed vial containing a predetermined quantity of a compound described in claim 1 and a reducing agent.

* * * * *